US008409602B2

(12) United States Patent
Messersmith et al.

(10) Patent No.: US 8,409,602 B2
(45) Date of Patent: Apr. 2, 2013

(54) SEALANTS FOR FETAL MEMBRANE REPAIR

(75) Inventors: Phillip B. Messersmith, Clarendon Hills, IL (US); Carrie Brubaker, Chicago, IL (US); Andreas H. Zisch, Zurich (CH); Corinne Zisch, legal representative, Zurich (CH)

(73) Assignees: Northwestern University, Evanston, IL (US); The University of Zurich, Zurich (CH)

( * ) Notice: Subject to any disclaimer, the term of this patent is extended or adjusted under 35 U.S.C. 154(b) by 264 days.

(21) Appl. No.: 12/845,949

(22) Filed: Jul. 29, 2010

(65) Prior Publication Data

US 2011/0027250 A1 Feb. 3, 2011

Related U.S. Application Data

(60) Provisional application No. 61/230,020, filed on Jul. 30, 2009, provisional application No. 61/231,108, filed on Aug. 4, 2009.

(51) Int. Cl.
A61F 2/00 (2006.01)
(52) U.S. Cl. ............... 424/423; 424/78.08; 424/668; 435/325; 435/371; 514/618; 514/916; 604/48
(58) Field of Classification Search ............ 424/423, 424/78.08, 668; 435/325, 371; 514/916, 514/619; 604/48
See application file for complete search history.

(56) References Cited

U.S. PATENT DOCUMENTS 6,350,463 B1 * 2/2002 Herman et al. ............... 424/425
2008/0247984 A1 * 10/2008 Messersmith et al. ...... 424/78.02

OTHER PUBLICATIONS

Bilic et al. Am. J. Obstetrics and Gyn. (Jan. 2010) 202: 85.e1-9.*
Definition of "amniotic" from thefreedictionary.com website downloaded Sep. 3, 2012 http://www.thefreedictionary.com/amniotic.*
Shapiro, et al., N. Engl. J. Med., 2000, 343:230-238.
Shapiro, et al., N. Engl. J. Med., 2006, 355:1318-1330.
Spotnitz, et al., Transfusion (Paris), 2008, 48:1502-1516.
Tatehata, et al., J. Appl. Polym. Sci, 2000, 76:929-937.
Van Der Windt, et al., Xenotransplantation, 2007, 14:288-297.
Van Der Windt, et al., Cell Transplant, 2008, 17:1005-1014.
Waite, et al., Ann. NY Acad. Sci, 1999, 875:301-309.
Waite, Science, 1981, 212:1038-1040.
Waite, et al., Biochemistry, 2001, 40:2887-2893.
Waite, Integr. Comp. Biol., 2002, 42:1172-1180.
Wang, et al., Biomaterials, 2007, 28:3456-3468.
Weber, et al., J. Biomed. Mater. Res. A, 2008, 90:720-729.
West, et al., Proc. Natl. Acad. Sci. USA, 1996, 93:13188-13193.
Westwood, et al., Macromolecules, 2007, 40:3960-3964.
Wilson, et al., Nano Lett, 2008, 8:1940-1948.
Yamada, et al., Biomacromolecules, 2000, 1:252-258.
Yin, et al., Biomaterials, 2009, 30:2764-2773.
Young, et al., Fetal Diagn. Ther., 2004, 19:296-300.
Yu, et al., Macromolecules, 1998, 31:4739-4745.
Yu, et al., J. Am. Chem. Soc., 1999, 121:5825-5826.
Yun, et al., Biomaterials, 2007, 28:1957-1966.
Zisch, et al., Swiss Med. Wkly., 2008, 138:596-601.
PCT International Search Report and Written Opinion, Application No. PCT/US2010/043679, Jul. 14, 2011.
Barshes, et al., J. Leukoc. Biol., 2005, 77:587-597.
Bennet, et al., Ups. J. Med. Sci., 2000, 105:125-133.
Brubaker, et al., Biomaterials, 2010, 31:420-427.
Burke, et al., Biomed. Mater., 2007, 2:203-210.
Burzio, et al., Biochemistry, 2000, 39:11147-11153.
Chang, et al., J. Pediatr. Surg., 2006, 41:905-909.
Chen, et al., Transplantation, 2006, 81:1421-1427.
Chen, et al., Transplantation, 2007, 84:122-125.
Cheung, et al., Bioconjug. Chem, 2006, 17:1036-1042.
Cortes, et al., Am. J. Obstet. Gynecol., 2005, 193:1197-1203.
Cruise, et al., Cell Transplant, 1999, 8:293-306.
De Groot, et al., J. Surg. Res., 2004, 121:141-150.
Deming, et al., Curr. Opin. Chem. Biol., 1999, 3:100-105.
Deprest, et al., Prenat Diagn, 2008, 28:878-880.
Devlieger, et al., Eur J. Obstet. Gynecol. Reprod. Biol, 2000, 92:145-150.
Devlieger, et al., Am. J. Obstet. Gynecol., 2006, 195:1512-1520.
Dufour, et al., Tissue Eng., 2005, 11:1323-1331.
Elsner, et al., Diabetologia, 2000, 43:1528-1533.
Ferland, et al., Hum. Reprod., 2001, 16:2718-2723.
Fritschy, et al., Transplantation, 1991, 52:777-783.
Gillinov, et al., J. Card. Surg., 2001, 16:255-257.
Gratacos, et al., Placenta, 2006, 27:452-456.
Harrison, et al., N. Engl. J. Med, 2003, 349:1916-1924.
Hill-West, et al., Proc. Natl. Acad. Sci. USA, 1994, 91:5967-5971.
Hu, et al., J. Am. Chem. Soc., 2003, 125:14298-14299.
Johns, et al., J. Am. Assoc. Gynecol. Laparosc., 2003, 10:334-338.
Lee, et al., Biomacromolecules, 2002, 3:1038-1047.
Lee, et al., Surg. Innov., 2005, 12:203-213.
Lee, et al., Proc. Natl. Acad. Sci. USA, 2006, 103:12999-13003.
Lee, et al., Science, 2007, 318:426-430.
Lee, et al., Nature, 2007, 448:338-341.
Leggat, et al., ANZ J. Surg., 2007, 77:209-213.
Liekens, et al., Prenat. Diagn, 2008, 28:503-507.
Louis-Sylvestre, et al., Am. J. Obstet. Gynecol., 1998, 178:287-293.
Mallik, et al., Obstet. Gynecol., 2007, 110:1121-1129.
McLaren, et al., Hum. Reprod., 1999, 14:237-241.
Merani, et al., Br. J. Surg, 2008, 95:1449-1461.
Mettler, et al., Fertil. Steril., 2004, 82:398-404.
Moberg, et al., Clin. Exp. Immunol., 2005, 142:125-131.
Notkins, J., Biol. Chem., 2002, 277:43545-43548.
Ochsenbein-Kolble, et al., Am. J. Obstet. Gynecol., 2007, 196:263 e1-7.

(Continued)

*Primary Examiner* — Susan Hanley
(74) *Attorney, Agent, or Firm* — Quarles & Brady LLP

(57) ABSTRACT

The present invention provides a method for preventing or repairing damage to a fetal membrane. In one embodiment, the method comprises contacting a fetal membrane with a composition comprising a four-armed catechol-terminated polyethylene glycol (cPEG) and a biocompatible oxidant. In one embodiment, the four-armed cPEG and the biocompatible oxidant are initially contained in separate solutions, and the solutions are mixed to form the composition just prior to or at the same time that the composition contacts the fetal membrane.

13 Claims, 12 Drawing Sheets

OTHER PUBLICATIONS

Oyen, et al., Am. J. Obstet. Gynecol, 2006, 195:510-515.
Papadopulos, et al., Fetal Diagn., 2006, 21:494-500.
Papov, et al., J. Biol. Chem., 1995, 270:20183-20192.
Petratos, et al., Lasers Surg. Med., 2002, 30:48-53.
Quintero, R.A., Clin. Perinatol., 2003, 30:573-589.
Quintero, R.A., Clin. Perinatol., 2001, 28:861-875.
Reddy, et al., Am. J. Obstet. Gynecol., 2001, 185:1090-1093.
Ryan, et al., Diabetes, 2005, 54:2060-2069.
Shag, et al., Macromol. Biosci., 2009, 9:464-471.

* cited by examiner a b

SEALANTS FOR FETAL MEMBRANE REPAIR

CROSS-REFERENCE TO RELATED APPLICATIONS

This application claims priority to U.S. Provisional Application No. 61/230,020, filed Jul. 30, 2009 and U.S. Provisional Application No. 61/231,108, filed Aug. 4, 2009, the entirety of both are hereby incorporated by reference herein for all purposes.

STATEMENT REGARDING FEDERALLY-SPONSORED RESEARCH OR DEVELOPMENT

The invention was made with government support under Grant Numbers R37 DE014193 and UL1 RR025741 awarded by the National Institutes of Health. The government has certain rights in the invention.

FIELD OF THE INVENTION

This invention is directed to novel sealants for membrane repair, specifically, to novel mussel-mimetic sealants for fetal membrane repair.

BACKGROUND OF THE INVENTION

Premature rupture of membranes (PROM) during the second and early third trimester of human pregnancy is often caused by rhexis or rupture of the amnion, especially in the area in contact with the uterine cervix. Rhexus of the amnion may be caused by physical weakening of the amnion, elevation of intrauterine pressure, and dilation of the cervix. Infection may accompany each of these conditions, all of which interact with each other.

Although the fetal membrane is normally very strong, it is possible for it to become mechanically fragile due to exposure to bacteria or infection. Resistance to infection depends on natural physiologic and mechanical barriers such as the endocervical mucus plug, intact fetal membranes and antimicrobial properties of amniotic fluid. PROM destroys those barriers. If PROM is left untreated, labor ensues, and the fetus is delivered with premature function of various organs. Therefore, it is desirable to prolong the gestation of the fetus.

Typically, a patient who has suffered premature membrane rupture is immobilized in bed and sometimes given a tocolytic agent and an antibiotic. This treatment has often not proved sufficient to prevent maternal and fetal infections or labor, thus still often resulting in premature birth. Thus, while the infusion of antibiotics and other agents may be helpful, it would be more effective to provide some sort of physical plug or barrier to ascending infection. Such a barrier would also prevent the leakage of amniotic fluid out of the amniotic sac and aid in prolonging the gestation.

The need for such a barrier or sealant for fetal membranes is especially important for iatrogenic preterm premature rupture of the fetal membranes (iPPROM). iPPROM often results as an adverse complication from fetal diagnostic or therapeutic interventions which may occur during the second and third trimesters of human pregnancy. These diagnostic and therapeutic interventions can be invasive, and can require surgery or other procedures with large diameter fetoscopes (an instrument inserted into the uterus for such things as visualizing the fetus, taking tissue samples, or performing fetal surgery). Such invasive techniques are frequently complicated by amniotic fluid leakage, separation of amnion and chorion, or even frank iatrogenic preterm premature rupture of the fetal membranes (iPPROM).

Fetoscopic procedures often have rates of iPPROM ranging between 6 to 45%,[1] although the iPPROM rates can me much higher. For instance, in a trial of fetal endoscopic tracheal occlusion for severe congenital diaphragmatic hernia, a 100% iPPROM rate was reported.[2] Since these procedures are usually performed in the second trimester of pregnancy, iPPROM usually occurs at an early gestational age, and can lead to premature birth of the baby or other serious complications to the mother and baby. Hence, the associated morbidity and mortality may compromise the expected benefits of the intervention. iPPROM is therefore a very serious complication for prenatal fetal surgery.

Clinically, measures of plugging membranes after established rupture as well as of preventive plugging of fetoscopic access sites have been undertaken, as reviewed previously.[3,4] Recent literature argues the risks and benefits of tocolytic agents, antibiotics, and corticosteroid injections primarily for delaying delivery, preventing intraamniotic infection, and enhancing fetal maturity, respectively, in the event of almost certain preterm delivery. However, to date, no true accepted treatment for iPPROM or PROM exists.

For closure after obvious iatrogenic rupture, intra-amniotic injection at the puncture site of maternal platelets mixed with fibrin cryoprecipitate ('amniopatch') has evolved as promising route to seal.[5,6] However, the sudden activation of a large number of platelets in the amniopatch was accounted for otherwise unexplained fetal demise in some cases.[5] But increasing efforts have been concentrated on taking prophylactic measures prior to rupture rather than therapy after established or symptomatic rupture of the membranes.

Several preventive plugging methods using dry collagen and gelatin plugs or liquid blood-derived sealants have already been clinically investigated.[7,8] Preliminary experience supports this prophylactic intervention for prevention of iPPROM. A 2006 report on a 27 patient cohort found a 4.2% rate of postoperative PPROM upon gelatin plug (Gelfoam) insertion upon port retrieval in endoscopic fetal surgery.[7]

In another small clinical study, sequential injection of platelets, fibrin glue and powdered collagen slurry directly to the puncture site successfully prevented amniotic fluid loss after endoscopic procedure.[8] Still, the positive outcome with these methods await to be reproduced in other centers. Of note, collagen fleece plugs (Lyostypt™) are now routinely used for prophylactic plugging of iatrogenic membrane defects following fetoscopic endoluminal tracheal occlusion for in utero therapy of congenital diaphragmatic hernia.

Other prophylactic plugging techniques such as scaffold-type plugs manufactured directly from decellularized amnion tissue have been so far only evaluated in animal models.[9,10] Further, laser welding, pre-emptive placement of synthetic surgical sealants before fetoscopic access, direct injection into amniotic fluid of fibrinogen/thrombin-based tissue sealant, and sealing with platelet-rich plasma were also evaluated in laboratory settings.[11,12,13,14]

Accordingly, there is a long-felt, unmet need for biocompatible, non-toxic and durable sealants for membrane repair that provide a physical barrier to amniotic fluid.

SUMMARY OF THE INVENTION

The present invention provides a novel and nonobvious method for preventing or repairing damage to a fetal membrane. In one embodiment, the method comprises contacting a fetal membrane with a composition comprising a four-armed catechol-terminated polyethylene glycol (cPEG) and a biocompatible oxidant. In one embodiment, the four-armed cPEG and the biocompatible oxidant are initially contained in separate solutions, and the solutions are mixed to form the composition just prior to or at the same time that the composition contacts the fetal membrane.

In one embodiment, the four-armed cPEG has the structural formula according to Formula I, wherein n is 55.

In some embodiments, the oxidant is selected from the group consisting of sodium iodate, Iron (III) chloride, a peroxide, oxygen, an inorganic base, an organic base, or an oxidase. In specific embodiments, the oxidant is a periodate such as sodium periodate.

In other embodiments, the composition further comprises an aqueous buffer solution, and in still further embodiments, the method further comprises the step of dissolving the four-armed cPEG in the aqueous buffer solution before the composition is contacted with the fetal membrane tissue.

In some embodiments, the step of contacting the fetal membrane with the composition is performed using a double barrel syringe mixer/applicator to mix and direct the composition onto the fetal membrane tissue. In such embodiments, before the composition is applied to the fetal membrane tissue, the solution containing the four-armed cPEG is added to one barrel of the syringe mixer/applicator, and the solution containing the oxidant is added to the other barrel of the mixer/applicator.

In one embodiment of the invention, the method is performed immediately before, during, or immediately after fetal endoscopic surgery.

In some embodiments, the composition is contacted with the fetal membrane at the endoscopic access site.

The invention also provides a method for transplanting islets onto a tissue surface. The method comprises the steps of (a) depositing one or more islets isolated from a donor pancreas onto a tissue surface; and (b) contacting the tissue surface with a composition comprising a four-armed catechol-terminated polyethylene glycol (cPEG) and a biocompatible oxidizing agent; whereby the islets are immobilized on the tissue surface. In one embodiment, the four-armed cPEG and the biocompatible oxidant are initially contained in separate solutions, and the solutions are mixed to form the composition just prior to or at the same time that the composition contacts the tissue surface. In one embodiment, the four-armed cPEG has the structural formula according to Formula I, wherein n is 55.

In some embodiments, the oxidant is sodium iodate, Iron (III) chloride, a peroxide, oxygen, an inorganic base, an organic base, or an oxidase. In other embodiments, the oxidant is a periodate such as sodium periodate.

In other embodiments, the composition further comprises an aqueous buffer solution.

In still other embodiments, the method of the present invention further comprises the step of dissolving the four-armed cPEG in the aqueous buffer solution before the composition is contacted with the fetal membrane tissue. In such embodiments, the step of contacting the tissue surface with the composition may be performed using a double barrel syringe mixer/applicator to mix and direct the composition onto the tissue surface. There, before the composition is applied to the tissue surface, the solution containing the four-armed cPEG is added to one barrel of the syringe mixer/applicator, and the solution containing the oxidant is added to the other barrel of the mixer/applicator. In some embodiments, the composition is contacted onto a tissue surface in vivo, while in other embodiments, the tissue surface is contained within a human or animal patient diagnosed with diabetes. In some embodiments, the tissue surface is an epidymal fat pad or a liver surface.

DETAILED DESCRIPTION OF THE INVENTION

Figure 1:
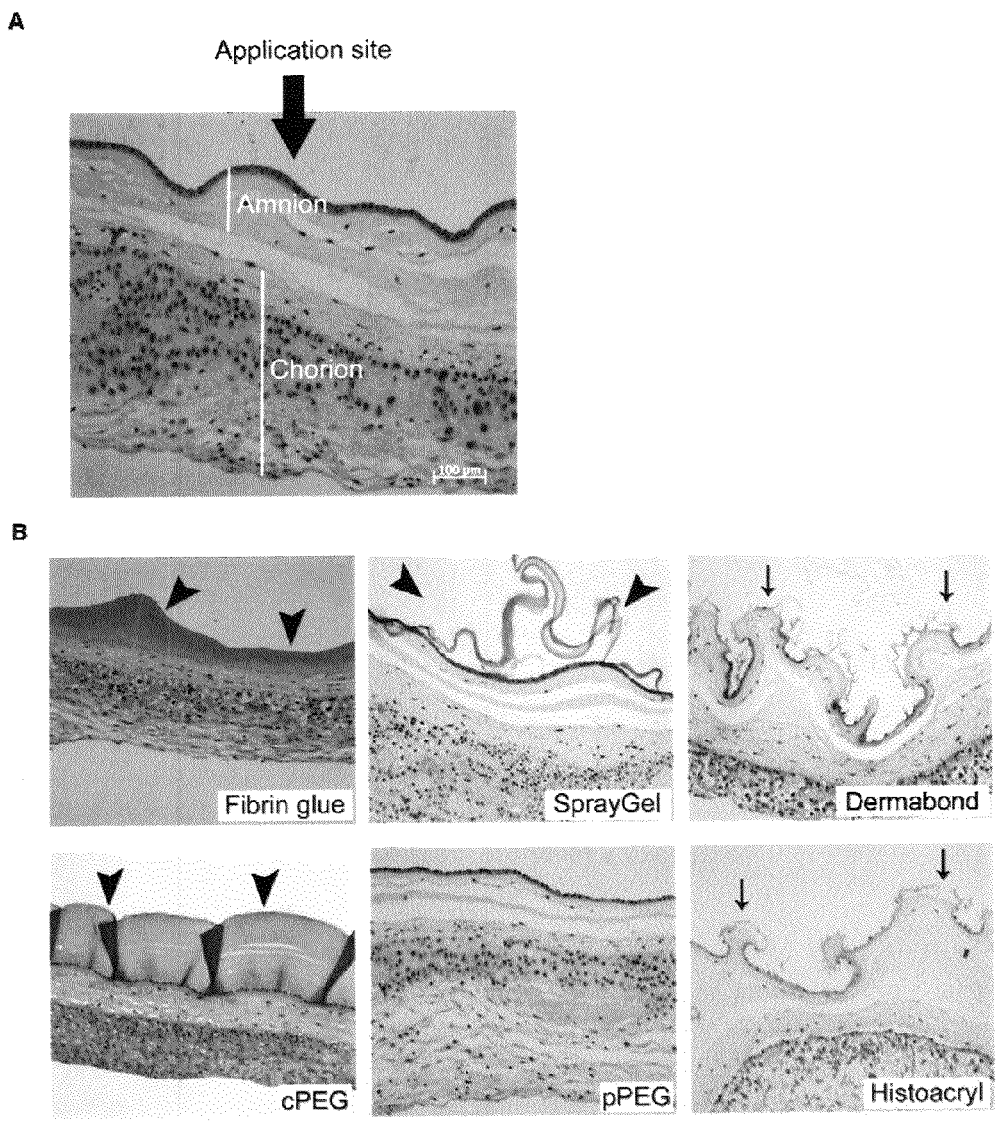
FIG. 1. Histologic assessment of bonding properties and effect for membrane morphology of bioadhesives. (A) Sealants were applied on the amniotic site of fetal membranes. (B) Images of hematoxylin/eosin-stained cross-sections of fetal membranes that were incubated with sealants for 24 h. Fat arrows mark the hydrogels, thin arrows mark the damage to the amnion layer by Dermabond and Histoacryl. Bar size: 100 µm.

The present invention provides novel biocompatible sealants for membrane repair, methods of synthesis and methods of use thereof. While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel sealants of the present invention are to be regarded as illustrative in nature and not restrictive.

I. In General

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides novel biocompatible sealants for membrane repair, methods of synthesis and methods of use thereof.

An emerging notion is that spontaneous healing appears slow, if not absent, in human fetal membranes. Histological follow-up of fetoscopic puncture defects in membranes of human patients several months after the procedure showed that the defects did not close by growth of new tissue.[15] The amnion layer contains few cells and does not contain blood vessels, which makes healing response in this layer unlikely.

Trials in rabbits of prophylactic plugging of membrane defects with decellularized amnion scaffolds showed effective sealing without detectable signs of biological repair after a 1-week period,[9] which is the maximum achievable in this experimental model. Recent studies in the midgestational rabbit observed signs of early healing of membrane defects upon addition of platelets or amniotic fluid cells to collagen plugs;[16,17] it is unclear whether this effect could assume relevant degrees of healing long-term.

Accordingly, a preferred prophylactic sealant material may present an immediate, non-toxic and durable physical barrier to amniotic fluid, and not necessarily induce biological healing of the defect. With this strategy in mind, we examined five liquid synthetic sealants, namely two types of cyanoacrylate glues and three poly (ethylene glycol-based) hydrogel-type polymers, for their principal aptitude for fetal membrane repair. Repair of defective tissue in moist/wet conditions or even underwater presents a particular challenge.

The present invention therefore provides a novel and non-obvious method for preventing or repairing damage to a fetal membrane. In one embodiment, the method comprises contacting a fetal membrane with a composition comprising a four-armed catechol-terminated polyethylene glycol (cPEG) and a biocompatible oxidant. In one embodiment, the four-armed cPEG and the biocompatible oxidant are initially contained in separate solutions, and the solutions are mixed to form the composition just prior to or at the same time that the composition contacts the fetal membrane. In one embodiment, the four-armed cPEG has the structural formula according to Formula I, wherein n is 55.

By "preventing" damage we mean protecting a fetal membrane from structural or chemical harm. By "repairing" damage, we mean correcting previously incurred structural or chemical harm. By "fetal membrane" we mean any membrane that functions for the protection or nourishment or respiration or excretion of a developing fetus, including without limitation the amnion, amnios, amniotic sac, chorion, allantois, embryonic membrane, caul, veil, tissue layer, umbilical or umbilical cord membranes.

By "biocompatible" we mean a macromonomer that does not have toxic or injurious effects on biological systems and exhibits minimal local inflammatory response in surrounding tissues. One example of a biocompatible macromonomer is those described in U.S. Patent Application No. 2008/0247980, incorporated by reference herein for all purposes.

In some embodiments, the oxidant is selected from the group consisting of sodium iodate, Iron (III) chloride, a peroxide, oxygen, an inorganic base, an organic base, or an oxidase. In specific embodiments, the oxidant is a periodate such as sodium periodate. In other embodiments, the composition further comprises an aqueous buffer solution, and in still further embodiments, the method further comprises the step of dissolving the four-armed cPEG in the aqueous buffer solution before the composition is contacted with the fetal membrane tissue.

In some embodiments, the step of contacting the fetal membrane with the composition is performed using a double barrel syringe mixer/applicator to mix and direct the composition onto the fetal membrane tissue. In such embodiments, before the composition is applied to the fetal membrane tissue, the solution containing the four-armed cPEG is added to one barrel of the syringe mixer/applicator, and the solution containing the oxidant is added to the other barrel of the mixer/applicator.

In one embodiment of the invention, the method is performed immediately before, during, or immediately after fetal endoscopic surgery. In some embodiments, the composition is contacted with the fetal membrane at the endoscopic access site.

The invention also provides a method for transplanting islets onto a tissue surface. The method comprises the steps of (a) depositing one or more islets isolated from a donor pancreas onto a tissue surface; and (b) contacting the tissue surface with a composition comprising a four-armed catechol-terminated polyethylene glycol (cPEG) and a biocompatible oxidizing agent; whereby the islets are immobilized on the tissue surface. In one embodiment, the four-armed cPEG and the biocompatible oxidant are initially contained in separate solutions, and the solutions are mixed to form the composition just prior to or at the same time that the composition contacts the tissue surface. In one embodiment, the four-armed cPEG has the structural formula according to Formula I, wherein n is 55.

In some embodiments, the oxidant is sodium iodate, Iron (III) chloride, a peroxide, oxygen, an inorganic base, an organic base, or an oxidase. In other embodiments, the oxidant is a periodate such as sodium periodate. In other embodiments, the composition further comprises an aqueous buffer solution. In still other embodiments, the method of the present invention further comprises the step of dissolving the four-armed cPEG in the aqueous buffer solution before the composition is contacted with the fetal membrane tissue. In such embodiments, the step of contacting the tissue surface with the composition may be performed using a double barrel syringe mixer/applicator to mix and direct the composition onto the tissue surface. There, before the composition is applied to the tissue surface, the solution containing the four-armed cPEG is added to one barrel of the syringe mixer/applicator, and the solution containing the oxidant is added to the other barrel of the mixer/applicator. In some embodiments, the composition is contacted onto a tissue surface in vivo, while in other embodiments, the tissue surface is contained within a human or animal patient diagnosed with diabetes. In some embodiments, the tissue surface is an epidymal fat pad or a liver surface.

In an alternate embodiment of the invention, a kit for preparing and using the novel sealant for membrane repair of the present invention is provided. In one embodiment, the kit comprises a biocompatible sealant and instructions for use.

In one embodiment, the kit comprises a powdered form of at least one of the biocompatible sealant, wherein the sealant is hydrated by the user for immediate use, such as in a dual syringe device to form a precursor liquid that rapidly gels. Optionally, the kit may contain a solution for dissolving the sealant. In an alternate embodiment, the kit comprises a biocompatible sealant according to the present invention formulated, delivered and stored for use in physiologic conditions.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention. Alternatively, the instructional material can be shipped separately from the container or provided on an electronically accessible form on a internet website with the intention that the instructional material and the biocompatible hydrogel be used cooperatively by the recipient.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Sealant Membranes for Fetal Repair

In the present study, we addressed adhesion of sealants to moist, intact fetal membranes. Alkyl-cyanoacrylate glues were chosen on the basis of their well-known strong bonding to tissue, and their use as tissue adhesives in surgical and traumatic wound repair.[18] Our choice of three synthetic poly (ethylene glycol) (PEG)-based hydrogel sealants, photopolymerizable gel, mussel-mimetic adhesive and commercial SprayGel™ was based on data showing their interfacial bonding to various tissues, and the possibility to deliver them in minimally invasive liquid form for gelation in situ.[19-21] Two types of PEG-based hydrogels under present study, SprayGel™ and photopolymerized PEG, were already used clinically. SprayGel™ has been clinically used as bioabsorbable anti-adhesion bather in patients undergoing myomectomy.[22]

A clinically approved formulation of photopolymerized PEG hydrogel sealant, FocalSeal-L™ sealant, proved successful for closure of pulmonary air leaks in the lung occurring at cardiac operations.[23] For the experimental mussel-mimetic adhesive hydrogel formulation of the present study, no clinical data exist yet. Here we estimated applicability of these synthetic polymers as sealants on fetal membranes based on their bonding to fetal membranes and toxicity in vitro, using the biosurgical Tissucol™ fibrin glue sealant as internal reference.

Material and Methods

Membrane collection and amnion cell isolation. The Ethical Committee of the District of Zurich approved the protocol (study Stv22/2006). A total of 15 fetal membranes were collected with written patient consent from elective caesarean sections. Mean gestational age was 38±1 weeks in the absence of labor, preterm rupture of membranes, chorioamnionitis, or chromosomal abnormalities. Fetal membrane pieces of 150-200 $cm^2$ were collected. The fetal membanes were cut approximately 2 cm from the placental disc to avoid the 'zone of altered morphology' overlying the cervix that is considered to be a naturally predefined breaking site of the membranes.[24] Human amnion epithelial (hAEC) and amnion mesenchymal cells (hAMC) were isolated and cultured as described previously.[9]

Sealants. Alkyl-cyanoacrylate glue sealants: Dermabond (Ethicon Inc., Norderstedt, Germany) and Histoacryl (B. Braun GmbH, Tuttlingen, Germany) are 2-octyl cyanoacrylate monomer and n-butyl-2-cyanoacrylate monomer, respectively. The formulations possess syrup-like viscosity. These glue act through anionic polymerization of hydroxyl groups from the minute amounts of moisture normally present on actual surfaces that are glued, including biological surfaces. Indeed, cyanoacrylate glues are known to be extremely adhesive to tissue.[18] Water act as a catalyst to accelerate this polymerization. The polymerization oocurs within minutes after application to tissue. The resulting resin is water resistant. Both Dermabond and Histoacryl are marketed as topical skin adhesives to hold skin edges of wounds from surgical incisions. As specified by the manufacturer of Dermabond, it is not for application on wet wounds.

Hydrogel sealants. SprayGel™ (Confluent Surgical, Inc., Waltham, Mass.) is a sprayable anti-adhesion barrier polymer that consists of two synthetic liquid precursors that when mixed together, rapidly cross-link to form a solid absorbable hydrogel in situ. The first precursor is a modified polyethylene glycol (PEG) with terminal electrophilic esters groups while the other precursor solution contains PEG that has nucleophilic amine groups.[25] SprayGel™ is marketed outside the US for use in abdominal and pelvic surgical procedures. It has been clinically also tried to reduce adhesion formation after ovarian surgery.[21] SprayGel™ was deposited at the fetal membranes through the air pump-assisted SprayGel™ Laparoscopic Sprayer. The gel is formulated to remain adherent on the site of application for approximately five days whereafter it is absorbed by way of gradual hydrolysis.

Photopolymerized PEG hydrogel sealant (pPEG) was formed via in situ interfacial photopolymerization of PEG diacrylate precursor of average molecular weight 700 Da (Sigma) according to a previously described gelation protocol.[20] Fetal membranes were flushed with a tissue adsorbing photoinitiator eosin Y (1 mM in 10 mM 4-(2-hydroxyethyl) piperazine-1-ethanesulfonic acid, pH 7.4, 0.15M sodium chloride; (HEPES-buffered saline). Then solution containing 10% PEG diacrylate and the co-catalysts triethanolamine (13.2 µL/mL) and 1-vinyl-2-pyrrolidine (3.5 µL/mL) in HEPES-buffered saline was applied to the membranes and photopolymerized by irradiation at 480-520 nm and 75 mW/cm$^2$ for 1 min from a portable Cermax xenon fiber optic light source, CXE300 (ILC Technology Inc., USA).

The mussel-mimetic tissue sealant is a catechol-functionalized poly(ethylene glycol) (cPEG) whose molecules crosslink into a hydrogel by way of oxidation after addition of sodium periodate.[26] The composition and synthesis of cPEG is described elsewhere[27], incorporated by reference herein for all purposes. For gelation, equal volumes of the polymer precursor solution (300 mg/mL in phosphate-buffered saline (PBS)) and the cross-linking solution (12 mg/mL sodium periodate in water) were mixed using a dual syringe applicator device equipped with a blending connector with mixer (FibriJet; Micromedics, Inc., St. Paul, Minn.). Hydrogels prepared from cPEG polymer and its derivatives are expected to possess, the ability to secure very strong adhesion to almost any surface, even under wet conditions. The presence of catechol in cPEG sealant was inspired by the wet adhesive properties conferred by the catechol side chain of 3,4-dihydroxyphenylalanine (DOPA) amino acid, which is found in high concentrations in the foot proteins of marine or freshwater mussels.[28,29]

Tissucol™ Duo S fibrin glue (Baxter AG, Volketwil, Switzerland) is a biological two-component adhesive that forms by mixing of human plasma cryoprecipitate solution with thrombin solution. The chemical and physical polymerization of the main component of fibrin glue sealant, fibrinogen, mimics the last step of the natural blood clot formation. Fibrin glue is clinically widely applied as hemostatic surgical sealant or adjunct to suture.[30]

Toxicity tests. Toxicity of sealants for fetal membrane cells was evaluated using direct contact and elution tests, as per International Organization for Standardization (ISO) 10993-5 guidelines.

Direct contact cytotoxicity. Direct contact studies were performed with term fetal membranes obtained from three cases. The amniotic layer was chosen for sealant application (FIG. 1A) because this layer was proposed to be the strength-bearing layer of fetal membranes and major determinant for PPROM.[31] 2×1 cm patches of freshly harvested fetal membranes were placed into wells of 6-well plates with amnion layer up. The sealants were applied at 50 µl and 200 µl volumes except cPEG adhesive which was only tested at 200 µl volume because of limited material. Membranes covered with sealant were covered with 3 mL culture medium (Ham's F-12/DMEM supplemented with 10% FBS, 100 U/ml penicillin, and 100 µg/ml streptomycin) and cultured for 24 h at 37° C. Controls were untreated membranes that were immediately processed for histology (control '0') or cultured for 24 h (control '24'). After 24 h, the treated membranes were fixed in 4% formaline, embedded in paraffin and sectioned for histology. Deparaffinized sections were either stained with hematoxylin-eosin (H/E), or stained for apoptotic cells using TUNEL technology (Terminal deoxynucleotidyl transferase dUTP nick end labeling; In Situ Cell Death Detection Kit, Fluorescein (Roche Diagnostics GmbH, Mannheim, Germany). For total cell counts, all cell nuclei were counterstained with 4',6-diamidin-2'-phenylindol-dihydrochlorid (DAPI; Sigma, Buchs, Switzerland). The histologic images were taken with a Zeiss Axiovert 200M fluorescent microscope (Carl Zeiss, Goettingen, Germany) equipped with an Zeiss AxioCam MRc digital camera and analysed with Axio-Vision Rel. 4.5 software (Carl Zeiss). Apoptotic and total cell counts were acquired from fluorescence micrographs using automated image analysis software ImageJ 1.34s (National Institute of Health, Bethesda, ML). One tissue section per case was analysed, taking four optical fields per section for analysis.

Elution toxicity. To test potential toxicity of soluble compounds released from the sealants for cultured amnion cells, two types of extractions were performed: First, extracts from sealant alone. For that, 0.2 mL of glue/hydrogel were incubated for 24 h in 3 mL Ham's-F12/DMEM/FCS culture medium. Second, extracts from sealants applied to membranes. The second method was to resolve whether treatment of membranes could result in production of cytokines by hAECs and hAMCs that add to induction of apoptosis. For that 0.2 mL glue/hydrogel sealant were applied to 2×1 cm pieces of fetal membranes and incubated for 24 h in 3 mL Ham's-F12/DMEM/FCS culture medium. The extracts were collected and stored at −80° C. until use for culture. Amnion cells from four human cases were subjected for assay of toxicity, and for each sealant the extraction test was evaluated in triplicate. 2×10$^4$ hAECs or hAMSCs were seeded per well of 48 well plates and cultured in Ham's/F12/DMEM/FCs standard medium near to confluence. Then medium was removed, and cells overlaid with 0.4 mL of extracts from either sealant alone, or extract from membranes/sealant combination. Extracts from untreated membrane samples from the same patients in standard culture medium served as controls. The cells were cultured for 72 h. Cell morphology was assessed microscopically, and degree of cell detachment and lysis was judged qualitatively.

The following evaluations were performed: (i) For total cell count, hAECs and hAMSCs were stained with DAPI (ii) Apoptotic cells were detected with in situ Cell Death Detection Kit (Roche Diagnostics GmbH). Total cell counts and apoptotic cell counts were acquired from fluorescence fluorescence micrographs using automated image analysis software ImageJ 1.34s (National Institute of Health, Bethesda, ML). (iii) Areas of individual cells were measured using LeicaQ Win Image Analysis software (Leica Imaging System Ltd, Cambridge, UK). (iv) Live/dead cell staining was performed. For that, amnion cell cultures were incubated for 3 min with a mix of calcein to detect live cells and ethidium-bromide homodimer to detect dead cells at 1 µM and 2 µg/ml, respectively. All experiments were performed in triplicates and four optical fields were analysed for each sample.

Sealing of fetal membranes lesion in vitro. Sealing performance of cPEG adhesive was tested on trocar punctures through fresh fetal membranes. For that, wet fetal membranes were flat-mounted with the amnion side up on a commercial motorized mechanical stretch device named 'The Cellerator™' (Cytomec GmbH, Switzerland; http://www.cytomec.com/) that we further adapted for use in fetal membrane studies (FIG. 3A). The Cellerator device permits expansion of fetal membranes expansion in a quasi-isotropic fashion, with points of attachment distributed in a near-circular pattern around the mounted membrane. While mounted in this device, membranes were continually kept moist with PBS. Puncture lesions were created with a three-side pointed Ø 3.5 mm trocar (Richard Wolf GmbH, Knittlingen, Germany), and approximately 0.5 mL cPEG adhesive was applied over the membrane defect. Two minutes after treatment, membranes were further stretched by about 30% of their original area. To demonstrate leak-proof sealing, the stretched membranes, still mounted in the device, were overlaid for 10 min with 0.3 L water. After the leak-proof test, the area of the treated membrane defect was excised and processed for standard histology. Histologic sealing was estimated microscopically from hematoxylin/eosin stained sections by the ability of the sealant to form a continuous bridge between the wound edges.

Statistical analysis. Data are shown as mean±SEM. Two-tailed unpaired t test was performed using GraphPad Prism version 4.00 for Windows (GraphPad Software, San Diego, Calif., USA). Significance level was set at $p<0.05$.

Results

Contact-mediated effect of sealants for membrane morphology. Histology illustrates the effect of treatment for overall membrane morphology for the six bioadhesives under test. Fibrin™ glue and cPEG adhesive formed a continuous layer tightly bound to tissue (FIG. 1B, arrow heads). The normal membrane morphology appeared maintained, with the amnion epithelial layer intact. SprayGel™ and pPEG exhibited partial or no binding to tissue, respectively. In the case of pPEG, we found the hydrogel layer sloughed into the culture medium shortly after immersion of the membranes in culture medium. Binding of Dermabond™ and Histoacryl to fetal membranes resulted in disruption of the amnion layer and change of overall membrane morphology, which was more pronounced for Dermabond™. The effects of 50 µl treatment volumes were very similar (not shown).

Figure 2:
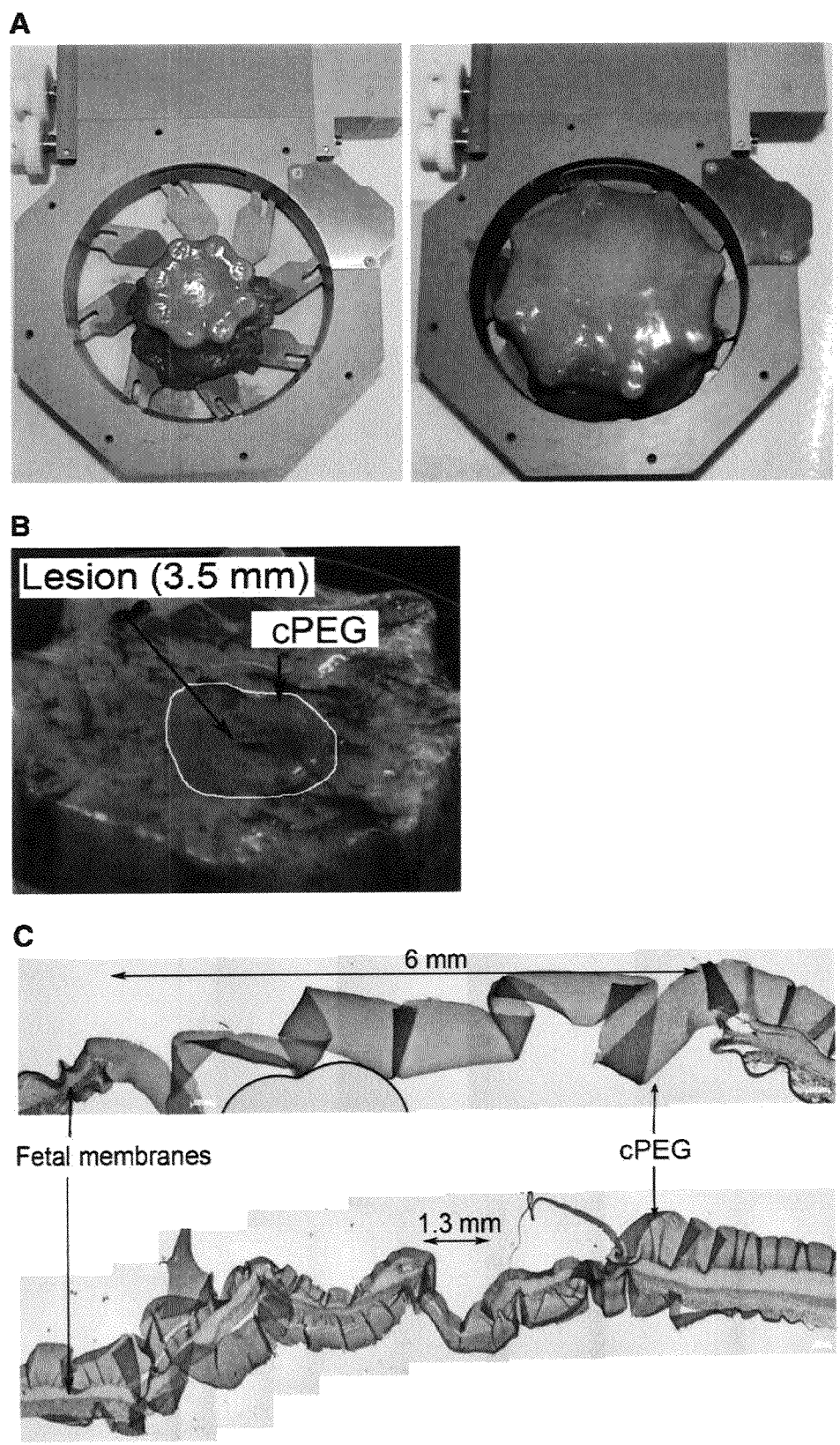
FIG. 2. Direct contact-mediated cytotoxic effect of sealants for fetal membranes. (A) Fluorescence micrographs of apoptotic cells (green) and total cells (DAPI). The example shows a section of a membrane treated with Dermabond. (B) Apoptosis rates in membranes treated with 200 µl sealant volumes. (C) Apoptosis rates in membranes treated with 50 µl sealant volumes. Values are mean±SEM. * indicates p<0.05.

Direct contact-induced apoptosis. We estimated acute toxic effects of sealants by measuring apoptosis in fetal membranes after 24 h of direct contact with sealants. FIG. 2A depicts fluorescence micrographs of apoptotic cells (TUNEL) and all cell nuclei in tissue (DAPI) in fetal membranes treated with Dermabond™. FIG. 2B gives the apoptosis rates for the 200 µl test series. In untreated reference membranes, the apoptosis rate increased to 17±2% during the 24 h incubation. Treatment with fibrin glue, cPEG adhesive, and pPEG did not enhance apoptosis over control. Dermabond™ and SprayGel™ treatment significantly ($p<0.05$) enhanced apoptosis by 3.9-fold to 69±13% and by 1.9-fold to 34±3% over the control, respectively. Histoacryl treatment produced a 1.6-fold increase of apoptosis rate to 28±6%, which was not significant over control. The outcome in the 50 µl test series was similar, except that at lower dose, the apoptosis rate by SprayGel was not significantly over control (FIG. 2C).

Elution toxicity of sealants for primary cultures of amnion cells. To test for toxicity from compounds released from the sealants, we investigated cell lysis, cell detachment and change of cell shape in hAECs and hAMCs that were grown in extracts of sealants in culture medium. None of the cultures, except those grown in extracts of Dermabond™, appeared affected by toxic compounds after 24 h and 72 h. There was no difference between extracts prepared from sealant alone, or from sealants applied to membranes. hAMSC were not affected in any condition as estimated by cell size and cell number. Only in the condition of hAECs grown in Dermabond™, we observed modest, insignificant reduction of cell size and number. Cell size of hAECs cultured in Dermabond™ extracts were 1138±166 µm$^2$ (n=193 cells) versus 1423±196 µm$^2$ (n=168 cells); cell numbers in the Dermabond™ condition were lower (323±31 cells/optical field) compared to control cultures (424±47 cells/optical field). TUNEL staining of hAEC and hAMC cultures did not show any induction of apoptosis, and live/dead staining with calcein and ethidium bromide showed that practically all cells in culture were alive. Overall, extracts of sealants behaved non-toxic for amnion primary cultures.

Figure 3:
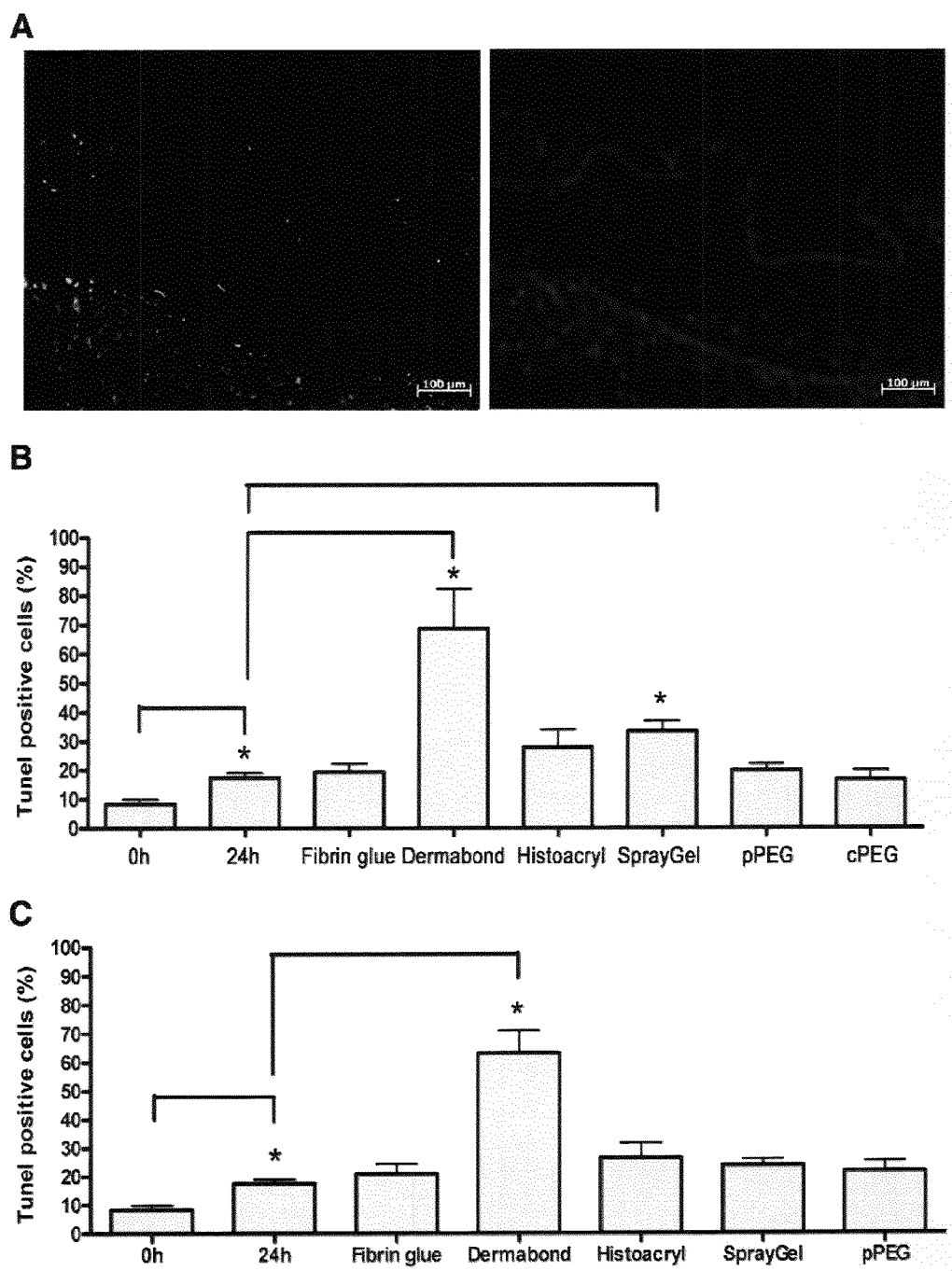
FIG. 3. Ex vivo sealing of fetal membrane defects with mussel-mimetic adhesive. (A) Fetal membranes mounted in a computerized radial stretch device before and after stretch. (B) Through-thickness puncture wounds (arrow) were created on fresh fetal membranes with a Ø 3.5 mm trocar. Approximately 0.5 mL of adhesive was applied over the defect. The white line marks the area of sealant. (C) Hematoxylin/eosin stained cross-section of a trocar puncture treated with cPEG adhesive. The hydrogel appears as ribbon-like structure that bridges the puncture edges. The bottom image shows a cross-section of the same lesion at a narrow location.

Sealing of puncture lesions in vitro. Our stratification revealed that cPEG adhesive and Tissucol fibrin glue both show strong bonding to fetal membranes and behave non-toxic, which are two basic prerequisites for prospective application for repair. cPEG adhesive is a new formulation that has never been tested for sealing of membrane defects before. We tested 0.5 mL cPEG adhesive for closure of Ø 3.5 mm trocar puncture wounds in fetal membranes mounted in a biomechanical test device (FIG. 3). Successful closure was achieved in all three test cases. Application of cPEG tissue adhesive over the defect resulted in an immediate leak-proof membrane seal that remained functional upon further radial stretch of the membranes. FIG. 3C shows representative histologic images from two locations of a puncture lesion sealed with cPEG tissue adhesive. Histology confirmed that the cPEG tissue adhesive connected the wound edges over a distance of approximately 6 mm, which was the maximum diameter in such lesions. cPEG tissue adhesive was found adhered to both the amnion side, the application side in these experiments, and also to the chorionic side of the membranes, Thus, sealant apparently passed through the lesion and spread underneath the membranes.

Discussion

Three commercial and two experimental synthetic sealants were tested along with Tissucol™ fibrin glue for applicability on fresh, moist human fetal membranes, using interfacial bonding and cytotoxicity after a 24 h direct contact duration in vitro for performance assessment. Four of the five synthetic sealants failed to meet the combined requirements of membrane bonding and non-toxicity which excludes them for this type of repair. Our screen identifies one synthetic hydrogel, cPEG tissue adhesive, that exhibits bonding to membranes and non-toxic characteristics that favorably compare to fibrin glue. cPEG adhesive demonstrated repair capacity for 3.5 mm trocar punctures, accomplishing immediate leak-proof sealing, which may warrant further evaluation in vivo.

Membrane bonding properties of the six bioadhesives under this study demonstrated large variability. Cyanoacrylate-based glues seem inappropriate for application on fetal membranes. The observation of their strong bonding to fetal membrane tissue was accompanied by obvious damage to the amnion epithelial layer and disruption of membrane structure, especially the amnion layer. Amniotic integrity is considered more important than chorionic integrity because the amnion is thought to have greater tensile strength.[31] In addition, Dermabond™, but not Histoacryl™, exhibited significant cytotoxicity. Two of the PEG-based hydrogel polymers, photopolymerizable PEG hydrogel and SprayGel™, failed to bond to fetal membranes sufficiently. Photopolymerized PEG-diacrylate hydrogels were previously used to create thin intravascular barriers to block thrombus deposition after balloon-induced arterial injuries in animal models, and firm adhesion of the PEG-diacrylate hydrogel to arterial walls was reported.[20,32] Although the pPEG and SprayGel™ hydrogels could: be polymerized on fetal membranes, they sloughed off from the membranes quickly after the immersion of the membranes in culture medium. Neither the hydrogel itself nor the one minute laser irradiation required for hydrogel curing produced adverse effects for membrane integrity. In the case of SprayGel™, the resulting polymer layer was discontinuous, weakly bonded to membranes, and cytotoxic.

cPEG adhesive, on the other hand, displayed membrane bonding and compatibility comparable to that of Tissucol fibrin glue. cPEG adhesive is a two-component, self-crosslinking polymer with the remarkable property to form strong and durable bonds to many surfaces even in wet environment. Creation of cPEG adhesive has been inspired by the composition of liquid adhesives secreted by marine mussels, which allow these organisms to firmly anchor themselves to any surface. The wet adherence of native mussel adhesive proteins rests on the unusual amino acid residue 3,4 dihydroxyphenylalanine (DOPA) that is present in high concentrations in the foot proteins of mussels.[28,33,34] The inventors have demonstrated that the wet adherence ability of mussel foot proteins can be conferred onto synthetic polymers by way of incorporating DOPA and DOPA analogues.[19,26,35,36] Indeed, previous work has demonstrated that DOPA-functionalized PEG precursors cross-link via sodium periodate-mediated oxidation to form adhesive hydrogels with high rigidity.[26]

In the present study, the cPEG polymer contains a simplified mimic of DOPA in the form of a reactive catechol group, generating a new variation of the adhesive that can be used under the same preparative conditions.[27] This formulation possesses both appealing and potentially problematic characteristics for use as a fetal membrane sealant. Properties that we consider favorable are fast gelation (under a minute); very slow hydrolysis over several months, allowing for durable sealing; and excellent tissue adhesion. Recent analysis revealed that bonds formed by a mussel-mimetic adhesive between porcine dermal tissues were several times stronger than those formed by fibrin glue.[19] Possible disadvantages of the present formulation are the use of the strong oxidizing reagent sodium periodate as trigger of polymerization, which is known to be strongly irritating. However, a rapid chemical reaction ensues upon contact of periodate with pPEG, which ultimately gives rise to chemical crosslinking of the polymer but also results in reduction of periodate to less harmful oxidative species.[19] Our estimates of direct contact cytoxicity were obtained after 24 h, which is the minimal contact duration for assessment according to the ISO 10993-5 test guidelines. Additional studies with extended contact between fetal membranes and cPEG sealant in organ culture in vitro[37] and in animal models will be necessary to establish long-term safety for membrane sealing. Issues of in vivo irritation and inflammatory tissue response to cPEG adhesive are currently addressed in another study involving the use of cPEG for transplantation of mouse islets.[27] While the results of that study in mice, like the in vitro data reported herein, reveal favorable biocompatibility, ultimately the full effects of cPEG on uterine contractions and fetal survival and integrity will require further evaluation in the pregnant rabbit model. Of further note, the present study was performed with membranes from the third trimester of pregnancy, while operative fetoscopy is usually performed in the second trimester. Membranes of earlier gestation could exhibit different reactivity to sealants and further testing on such membranes will be necessary.

In summary, the present invention provides a novel synthetic hydrogel mussel-mimetic sealant with appealing properties for membrane sealing.

Example 2

Mussel-Inspired Adhesive in Extrahepatic Islet Transplantation

There is significant need for effective medical adhesives that function reliably on wet tissue surfaces with minimal inflammatory insult. To address these performance characteristics, we have generated a synthetic adhesive biomaterial inspired by the protein glues of marine mussels. In-vivo performance was interrogated in a murine model of extrahepatic syngeneic islet transplantation, as an alternative to standard portal administration. The adhesive precursor polymer consisted of a branched poly(ethylene glycol) (PEG) core, whose endgroups were derivatized with catechol, a functional group abundant in mussel adhesive proteins. Under oxidizing conditions, adhesive hydrogels formed in less than 1 min from catechol-derivatized PEG (cPEG) solutions.

Upon implantation, the cPEG adhesive elicited minimal acute or chronic inflamematory response in C57BL6 mice, and maintained an intact interface with supporting tissue for up to one year. In-situ cPEG adhesive formation was shown to efficiently immobilize transplanted islets at the epididymal fat pad and external liver surfaces, permitting normoglycemic recovery and graft revascularization. These findings establish the use of synthetic, biologically-inspired adhesives for islet transplantation at extrahepatic sites.

Robust adhesion and cohesive integrity represent valuable characteristics of a medical adhesive, especially for applications requiring long-term performance of the material. However, limitations of currently approved synthetic adhesives include poor adhesion in the presence of biological fluids, sensitization and allergic response, and inflammation. Overcoming these performance deficiencies requires a material that is easily administered in a clinical environment, reliably and durably bonds to target tissue surfaces in a wet environment, has sufficient cohesive strength, and stimulates minimal local or systemic inflammatory insult.

To generate such a material, we have taken inspiration from the remarkable adhesive capabilities of the marine blue mussel *Mytilus edulis*. Mussel adhesive proteins that comprise the secreted *M. edulis* foot pad are enriched in the post-translationally modified amino acid 3,4-dihydroxy-phenylalanine (DOPA). Subsequent to secretion of the liquid protein precursor, oxidation of the DOPA catechol side chain leads to intermolecular coupling reactions among the mussel adhesive proteins and in-situ hardening of the mussel foot pad.

Adhesion to the target surface is also mediated by DOPA, in the form of a variety of strong noncovalent and covalent chemical interactions with solid substrates. Motivated by the belief that catechol incorporation into synthetic polymers will enhance wet adhesive properties, we as well as others have investigated catechol-containing linear or branched synthetic polymers as mimics of mussel and other marine adhesives. Although in vitro evaluation of tissue biocompatibility and adhesion have been reported, in vivo performance of these candidate medical adhesives has not been investigated. The purpose of this work was to demonstrate mussel-inspired adhesive performance in vivo, with an emphasis on tissue biocompatibility and integrity of the adhesive/tissue interface.

To this end, biomimetic cPEG adhesive performance was interrogated in a murine animal model of islet transplantation, for the amelioration of diabetes. In humans, type I diabetes mellitus is an autoimmune disease resulting from autoreactive T-lymphocyte-mediated destruction of pancreatic islet beta cells. Select patients can be treated by replacing lost beta cell function through whole islet transplantation. The standard methodology of human clinical islet transplantation was successfully established by the Edmonton protocol, which calls for intrahepatic islet delivery to the liver vasculature via portal vein cannulation.

However, islet contact with whole blood results in an instant blood-mediated inflammatory response (IBMIR), characterized by platelet and complement activation, neutrophil and monocyte infiltration, and decreased islet viability. Furthermore, activation of liver resident macrophages (Kupffer cells) initiates release of toxic cytokine mediators IL-1b, IL-6, and TNF-a, as well as reactive oxygen species superoxide, hydrogen peroxide, and nitric oxide, with adverse consequences on islet function. Following treatment according to the Edmonton protocol, these effects may compromise islet engraftment and contribute to a gradual decrease in long-term graft survival.

As a result, there is significant interest in alternative, extrahepatic tissue sites for experimental and clinical islet transplantation. To avoid the functional impairment associated with intrahepatic portal infusion, we propose a new islet transplantation paradigm involving direct immobilization of islets onto intraabdominal tissue surfaces, using a thin, tissue-adherent conformal hydrogel membrane. This 'islet sealant' approach offers the potential advantages of convenient, rapid, and minimally invasive islet transplantation by direct apposition of the islet bolus onto tissue surfaces. Further, the technique avoids the intravascular engraftment site, eliminating IBMIR and other adverse effects of first-pass blood exposure in the liver, while maintaining the capability of rapid islet revascularization and the benefits of direct insulin secretion into the portal circulation. Here, we illustrate the concept using a mussel-inspired adhesive polymer hydrogel in a functional model of murine islet transplantation to the epididymal fat pad and external liver surfaces.

Synthesis of cPEG mussel-mimetic adhesive precursor. 5.0 g four-arm PEG-amine (10 kDa; P4AM-10; SunBio, Anyang City, South Korea) was added to 2:1 chloroform:dimethylformamide. Following dissolution, 0.584 g (3.2 mmol) 3,4-dihydroxyhydrocinnamic acid (DOHA; Fluka, Steinheim, Germany), 0.432 g (3.2 mmol) N-hydroxybenzotriazole (HOBt; Advanced ChemTech, Louisville, Ky.), 1.21 g (3.2 mmol) HBTU (Novabiochem, San Diego, Calif.), and 680 mL (4.9 mmol) triethylamine (Sigma, St. Louis, Mo.) were added to the PEG-amine reagent solution.

After 1 h, the reaction solution was filtered and precipitated in cold anhydrous diethyl ether. The resulting white precipitate was collected and dried overnight under vacuum. The dried product was resuspended in 12 mM HCl, filtered, and transferred to dialysis tubing (3500 MWCO). Extensive dialysis was carried out in acidic water, pH 3.5-4.0. Aqueous dialyzed product was filtered, flash frozen, and lyophilized to yield the purified product. UV spectrometry (Abs280; model U-2010; Hitachi, San Jose, Calif.) confirmed DOHA modification of the PEG reagent, via interpolation of adhesive precursor catechol concentration against a DOPA standard curve. Degree of modification of the PEG starting material by DOHA was determined by 1H-NMR (INOVA 500 MHz; Varian, Palo Alto, Calif.) in deuterated chloroform. cPEG was ethylene oxide gas sterilized (AN74i Anprolene sterilizer; Andersen Sterilizers, Haw River, N.C.) on a 12-h cycle prior to in-vivo use.

Formation of cPEG adhesive hydrogels. cPEG adhesive precursor was dissolved in 2_phosphate-buffered saline at 300 mg/mL. An equivolume solution of 0.056 M sodium periodate (Sigma) in deionized water was added to induce gelation. Gelation time was determined by inversion method.

Material-only implantation. Healthy, age-matched male C57BL6 mice (Jackson Laboratories, Bar Harbor, Me.) were anesthetized with nebulized isoflurane (IsoThesia; Butler/Abbott Laboratories, North Chicago, Ill.) and intraperitoneal injection of 2% Avertin (2,2,2-tribromoethanol, Sigma) at 0.3 mg/g body weight, prior to shaving of the abdomen and sterile preparation of the surgical site. The left epididymal fat pad was exposed through midline lower abdominal incision and manipulation of the tissue flap. This thin, well-vascularized tissue is analogous to the omentum of larger mammals and has dimensions on the order of 1.5_1.5 cm. Sterile, two-component mixing and adhesive delivery was achieved by a dual-barrel blending connector with mixer device (Micromedics, St Paul, Minn.) containing sterile-filtered 300 mg/mL cPEG and 0.056 M sodium periodate, respectively.

Following topical delivery of approximately 100 mL adhesive, the deposition site was left undisturbed for 1 min. The sample site was then manually reinserted into the lower abdominal cavity and the incision closed with double-layer suture. Mice were monitored postoperatively until conscious recovery. At three days, two weeks, six weeks, and one-year post-implant, the adhesive and associated adipose tissue was surgically removed from anesthetized mice, prior to euthanasia. Samples were fixed overnight in 10% neutral-buffered formalin at 4° C. and mounted in paraffin. 4 mm tissue sections were subjected to hematoxylin and eosin (H&E) staining and visualized with standard light microscopy (Axioskop and AxioCam MRc5, with associated Axiovision LE imaging software; Zeiss, Jena, Germany). These and subsequent animal studies were performed with the approval and supervision of the Northwestern University Animal Care and Use Committee.

Diabetic induction. Five to seven days prior to transplant surgery, healthy, age-matched male C57BL6 mice were intraperitoneally injected with streptozotocin (Sigma) in 0.9% sodium chloride at 220 mg/kg body weight. Streptozotocin is a nitrosourea glucose analog that is specifically transported into beta cells by the GLUT2 receptor, where cytotoxic DNA alkylation ultimately results in diabetes. Recipient mice were considered diabetic following two non-consecutive days of non-fasting blood glucose measurements _300 mg/mL.

Blood glucose was analyzed on the One Touch BASIC glucose monitor (Lifescan, Milpitas, Calif.) from whole blood obtained by tail snip.

Donor islet isolation. Healthy, non-diabetic, age-matched male C57BL6 mice were anesthetized and prepared for surgery as above. The bile duct was clamped at the duodenal junction and cannulated for pancreatic perfusion of 3 mL 0.5 mg/mL cold collagenase (Type XI, from *clostridium histolyticum*; Sigma) in Hank's balanced salt solution (HBSS). Perfused pancreata were incubated at 37° C. with occasional agitation to promote tissue degradation. The digested tissue was suspended in HBSS þ 10% fetal bovine serum (FBS) and briefly centrifuged. The resultant pellet was resuspended and filtered through sterile mesh to remove bulk tissue matter. Centrifugation of the liquid filtrate yielded the islet-containing tissue pellet, which was subjected to Ficoll dextran discontinuous gradient centrifugation. Isolated islets were hand-picked from the gradient, combined, washed 3× with HBSS þ 10% FBS, counted, and cultured until use in CMRL-1066 þ 10% FBS, 1% penicillin/streptomycin, and 1% L-glutamine, at 37° C. with 5% $CO_2$.

Islet transplantation. Streptozotocin-induced diabetic mice were anesthetized and prepared for surgery as above. All recipients were syngeneically transplanted with 150 islets. For islet deposition at the epididymal fat pad or liver surfaces, each 150-islet sample was collected in clamped narrow gauge tubing and briefly centrifuged to compact the islet bolus. The tubing was attached to a constant rate syringe (Hamilton, Reno, Nev.), which permitted controlled islet delivery to the exposed tissue surface following clamp removal. In mice receiving islets at the epididymal fat pad with suture closing (n ¼7), the fatty tissue was folded over the islet deposition site and immobilized with a single suture.

For adhesive-mediated islet transplant at the epididymal fat pad (n ¼8), approximately 100 mL cPEG was applied following islet deposition directly on this tissue surface. The adhesive hydrogel was allowed to cure 1 min prior to tissue reinsertion into the lower abdominal cavity. Similarly, islets delivered to the liver lobe surface were immobilized with cPEG adhesive application (n ¼9). For intrahepatic portal control mice (n¼ 7), the 150-islet bolus was drawn into a 3 mL syringe and slowly injected into the liver vasculature following portal vein exposure and cannulation. Bleeding was controlled with discretionary application of Avitene (microfibrillar collagen hemostat; Davol, Warwick, R.I.). In all experimental groups, incision sites were closed with double-layer suture, and mice were monitored post-operatively until conscious recovery.

Analysis of graft and adhesive performance. Transplanted mouse blood glucose was monitored in whole blood obtained from tail snip using One Touch BASIC glucose monitor. Recipient mice were considered normoglycemic upon non-fasting blood glucose<200 mg/dL. Recipient weight was simultaneously monitored to confirm normal weight gain and glucose management under fed conditions (data not shown). Intraperitoneal glucose tolerance test (IPGTT) was performed at 105 days post-transplant on recovered, normoglycemic recipients and healthy controls (n=5). Mice were fasted for 4 h, and water was removed for the duration of the test. 10% glucose (Hospira, Lake Forest, Ill.) at 2 g/kg body weight was injected intraperitoneally to initiate IPGTT. Blood glucose levels were monitored at baseline (30 and 15 min prior to injection) and every 15 min following injection for 3 h.

The integrated insulin response, defined by area under the blood glucose excursion curve, was calculated using the trapezoidal rule. At 112 days post-transplant, all groups except intrahepatic portal recipients underwent graft explant survival surgery, for graft analysis and to observe subsequent hyperglycemia. Mice were euthanized following return to the diabetic state. Similarly, one mouse transplanted at the epididymal fat pad with cPEG immobilization underwent graft explant for histological analysis at day 100 post-transplant; this mouse was not included in the intraperitoneal glucose tolerance test. The liver was isolated from intrahepatic portal recipients for histological analysis only, in a non-survival procedure at the termination of in-vivo studies (day 118).

Explanted tissues were fixed overnight in 10% neutral-buffered formalin at 4° C. and mounted in paraffin. 4 mm tissue sections were stained with hematoxylin and eosin (H&E) for standard light microscopic visualization. Immunohistochemical triple stain was performed to identify insulin, CD31, and OX-41 epitopes, for the visualization of functional islets, vascular endothelial cells, and macrophages, respectively. Slides were serially treated with guinea pig mouse-reactive anti-swine insulin (1° antibody, 200×, 1 h; Dako, Carpinteria, Calif.) and FITC-conjugated donkey anti-guinea pig (2° antibody, 200×, 30 min; Jackson ImmunoResearch Laboratories, West Grove, Pa.); rat anti-mouse CD31 (1° antibody, 100×, 1 h; Fitzgerald, Concord, Mass.) and Texas Red-conjugated donkey anti-rat (2° antibody, 200×, 30 min; Jackson ImmunoResearch Laboratories); and mouse-reactive mouse anti-rat OX-41 (1° antibody, 100×, 1 h; Millipore, Billerica, Mass.) and AMCA-conjugated goat anti-mouse (2° antibody, 200×, 30 min; Jackson ImmunoResearch Laboratories). Treated slides were visualized using standard fluorescence microscopy and RGB channels combined to generate triple-stain images (Axioskop and AxioCam MRc5, with associated Axiovision LE imaging software, Zeiss, Jena, Germany).

Statistics. All data are expressed as mean (±SEM). Statistical analysis of experimental groups was performed using one-way analysis of variance (ANOVA) and Tukey's multiple comparisons post-test. Statistical significance was defined as $p<0.05$. Normal distribution of the data was confirmed by the method of Kolmogorov and Smirnov.

Figure 4:
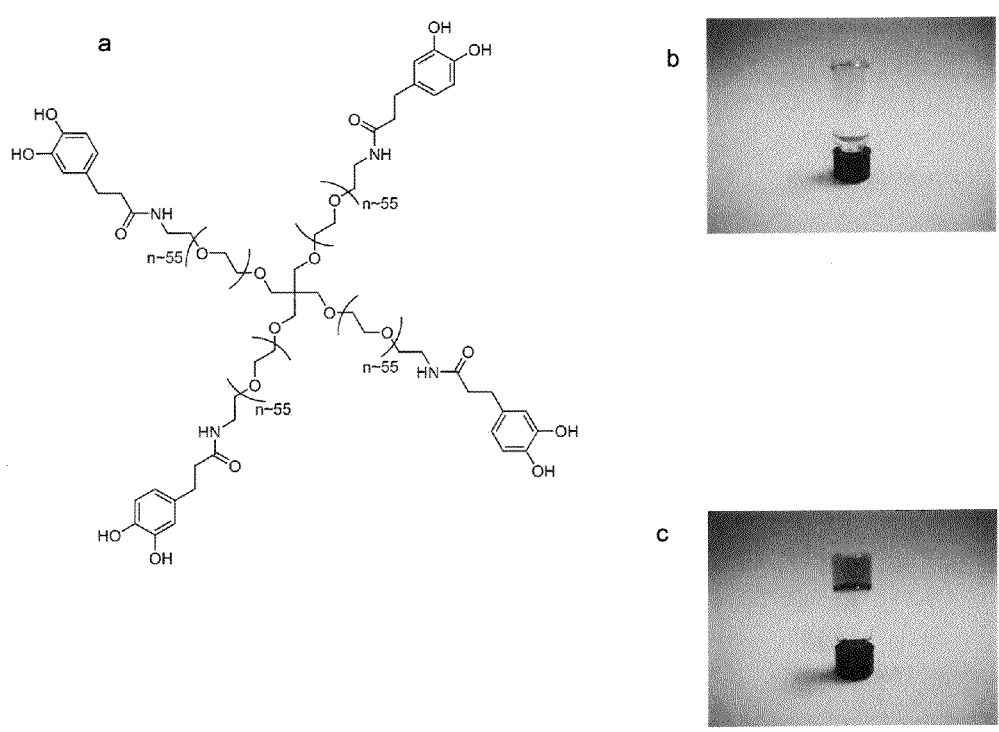
FIG. 4. Structure and gelation of the catechol-terminated cPEG adhesive precursor. (a) Chemical structure of cPEG adhesive precursor. Photographs of precursor solution in phosphate-buffered saline before (b) and after (c) addition of aqueous sodium periodate solution; gel formation occurred within 20-30 s.
Figure 10:
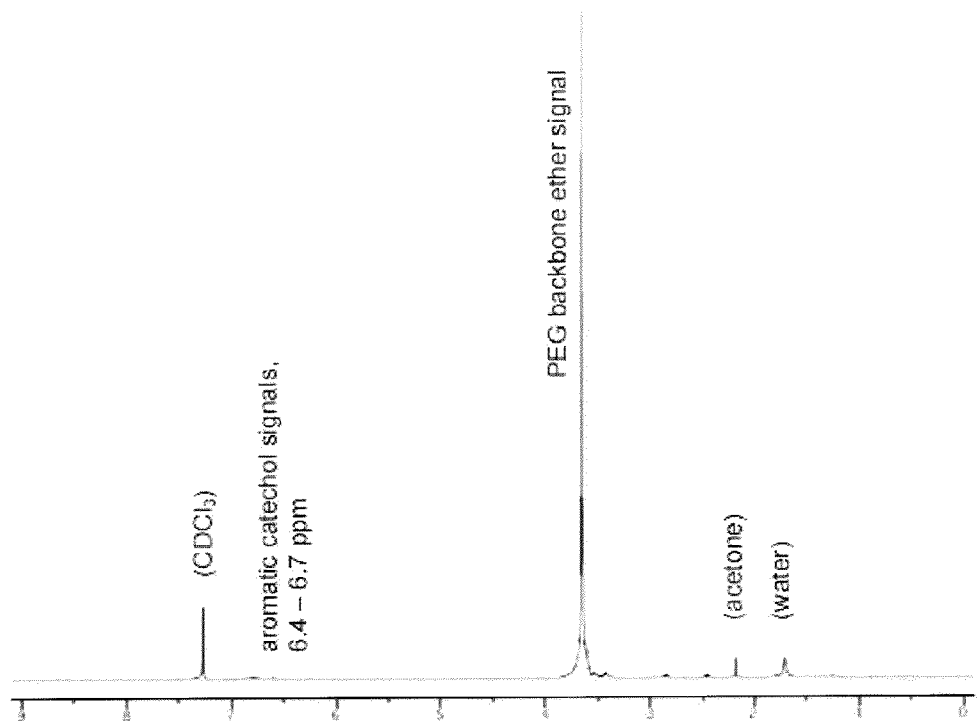
FIG. 10. 1H-NMR (500 MHz, CDCl3) of mussel-mimetic cPEG adhesive precursor polymer.

Results. Preparation of the cPEG precursor polymer and cross-linked adhesive hydrogel. To generate the adhesive precursor polymer, an amine-terminated four-arm poly(ethylene glycol) (PEG, 10 kDa) was modified with 3,4-dihydroxyhydrocinnamic acid (DOHA) through standard peptide chemistry. The resultant four-arm, catechol-terminated PEG (cPEG) adhesive precursor (FIG. 4a) was synthesized on the multigram scale, facilitating its use in animal studies. As determined by 1H-NMR (FIG. 4, FIG. 10) and UV spectrometry, there was 76% DOHA modification of the PEG starting material, with 0.4 mmol catechol per mg cPEG polymer. cPEG readily dissolves in relevant aqueous buffers such as phosphate-buffered saline, yielding a free-flowing transparent solution (FIG. 4b). Addition of aqueous sodium periodate solution induces gel formation and material color change from colorless to translucent brown (FIG. 4c). Using the literature as a guide, employing optimized cPEG and sodium periodate cross-linker solution concentrations provoked hydrogel formation within 20-30 s after mixing.

Figure 5:
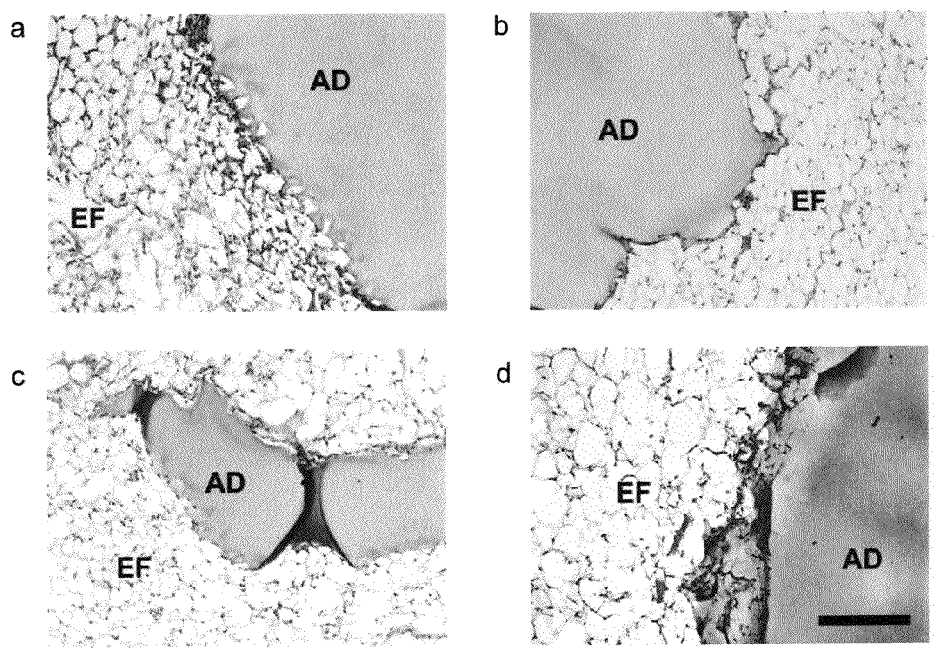
FIG. 5. Representative light micrographs of hematoxylin and eosin (H&E)-stained cPEG adhesive and mouse epididymal fat pad tissue samples removed at three days (a), two weeks (b), six weeks (c), and one year (d) after material-only implantation. Adhesive, AD; epididymal fat tissue, EF. All images, scale bar: 200 µm.

Evaluation of cPEG adhesive implantation at the murine epididymal fat pad. Healthy, untreated mice received 100-150 mL adhesive, expelled directly from a double barrel syringe mixer/applicator, on the flat surface of the epididymal fat pad. A thin conformal hydrogel membrane formed in under 1 min, after which manipulation by gentle depression, folding, and lavage did not interfere with gel integrity or adhesion to the underlying tissue. The adhesive produced no immediate visible inflammation or redness at the deposition site. Following surgery, all mice recovered normally and remained healthy over the course of the study. At three days, two weeks, six weeks, and one-year post-implantation, the adhesive/tissue sample was isolated for histological analysis (FIG. 5). In each sample, the adhesive, with uniform pink-purple hue, is attached to and surrounded by epididymal fat pad tissue, whose adipocyte cell membranes are stained in this technique. Little to no inflammatory cell infiltrate is observed at any time point, with little evidence of fibrotic capsule formation over time. Grossly, at all observed time points, the adhesive hydrogel material was visible and present at the original deposition site, and the material-tissue interface was intact. The surrounding adipose tissue was healthy and well vascularized, and there was no evidence of non-specific postsurgical adhesions.

Figure 6:
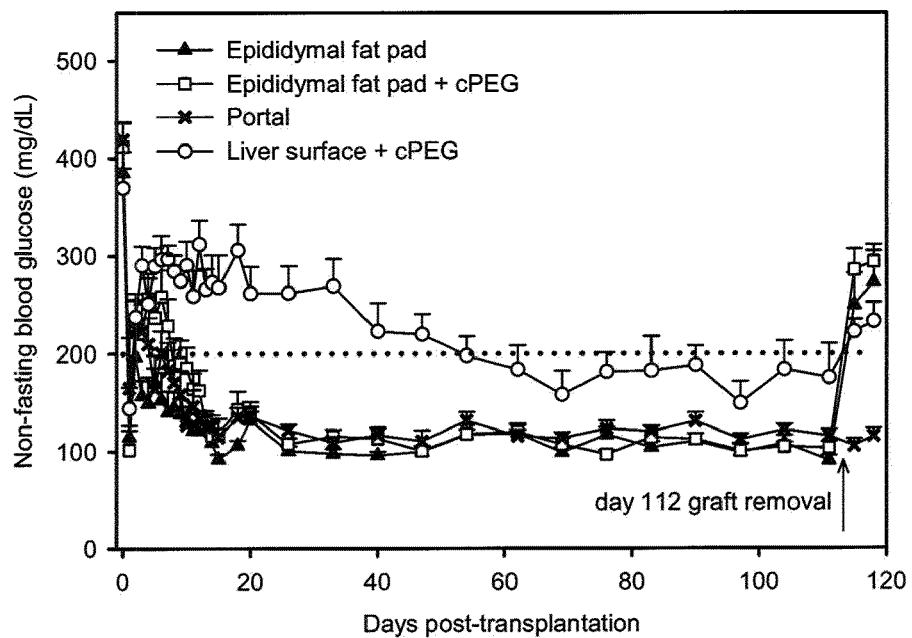
FIG. 6. Normoglycemic recovery following cPEG adhesive-mediated minimal islet transplantation. (a) Mean non-fasting blood glucose from day 0 (day of transplantation) to day 118 (day of euthanasia), in mice that received 150 islets at the sutured epididymal fat pad (▲, n=7); at the epididymal fat pad with adhesive immobilization (□, n=8); via intrahepatic portal delivery (x, n=7); and at the liver surface with adhesive immobilization (○, n=9). Normoglycemia is defined as non-fasting blood glucose<200 mg/dL (dotted line). Error bars represent standard error of the mean. (b) Percentage of diabetic recipients remaining within each group as a function of time, following 150-islet transplantation at the sutured epididymal fat pad (solid fine line), at the epididymal fat pad with adhesive immobilization (short dashed line), via intrahepatic portal delivery (solid bold line), and at the liver surface with adhesive immobilization (long dashed line). Asterisk (*) indicates statistical significance in the mean number of days to cure (with n=8) compared to all other groups (p<0.001).
Figure 6:
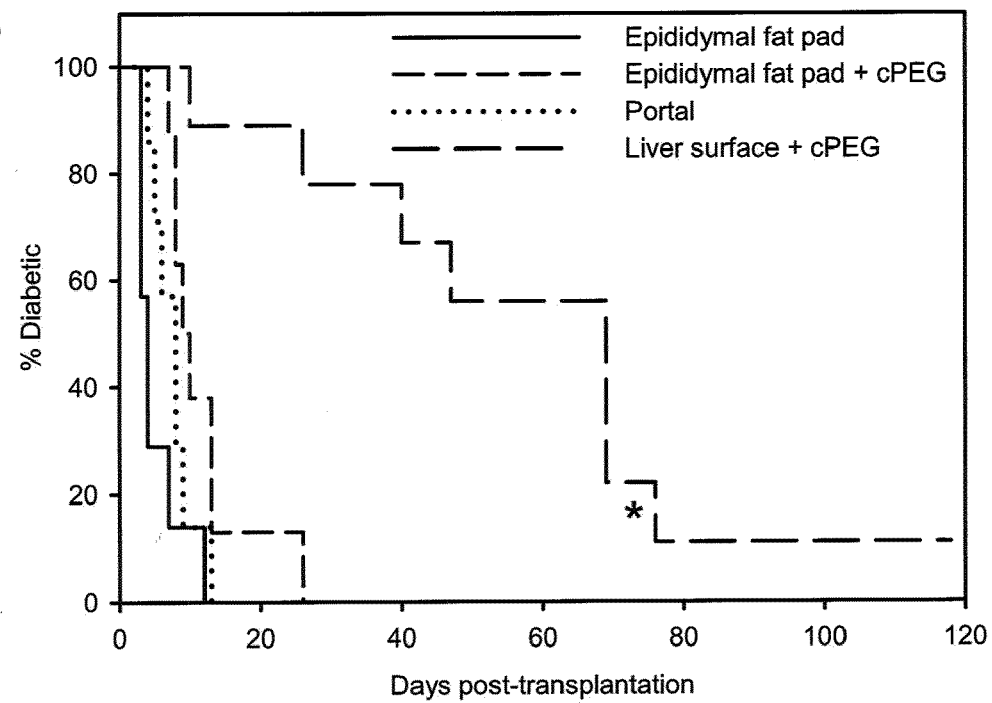

Outcome of cPEG-mediated syngeneic islet transplantation. Adhesive-mediated islet transplantation was performed at the epididymal fat pad and on the liver surface. At both sites, the cPEG adhesive formed a visible, translucent, thin hydrogel layer over the affixed islet bolus, resulting in islet entrapment between the adhesive and tissue surface. Two groups of control mice received 150 islets per mouse at the epididymal fat pad (single suture closure, no adhesive), or into the liver via hepatic portal vein cannulation. Islet transplant recipients recovered normally postsurgery. Blood glucose was monitored for four months following transplantation, as a measure of islet graft performance and adhesive biocompatibility (FIG. 6a). Between mice transplanted at the sutured epididymal fat pad, at the epididymal fat pad with cPEG adhesive immobilization, and via intrahepatic portal infusion, there was no statistical difference in the mean number of days post-transplant upon which normoglycemia was achieved. Islet engraftment to the external liver surface using cPEG adhesive required a significantly longer time to achieve normoglycemia than the three other groups (p<0.001, all cases). Kaplan-Meier survival curves highlight the outcome of islet transplantation for the various groups (FIG. 6b). Mice transplanted at the sutured epididymal fat pad regained normoglycemia at 5.1±1.3 days following surgery (mean±SEM), whereas mice transplanted intrahepatically via portal vein cannulation regained normoglycemia at 7.6±1.1 days. Further, all mice transplanted at the epididymal fat pad with cPEG-immobilized islets achieved normoglycemia, at a mean of 11.5±2.2 days. In the case of islet immobilization on the external liver surface, there was 89% success rate of normoglycemic induction (1 islet graft failure). This experimental group demonstrated a broader range of cure times, with a mean of 50.8±8.5 days.

Figure 7A:
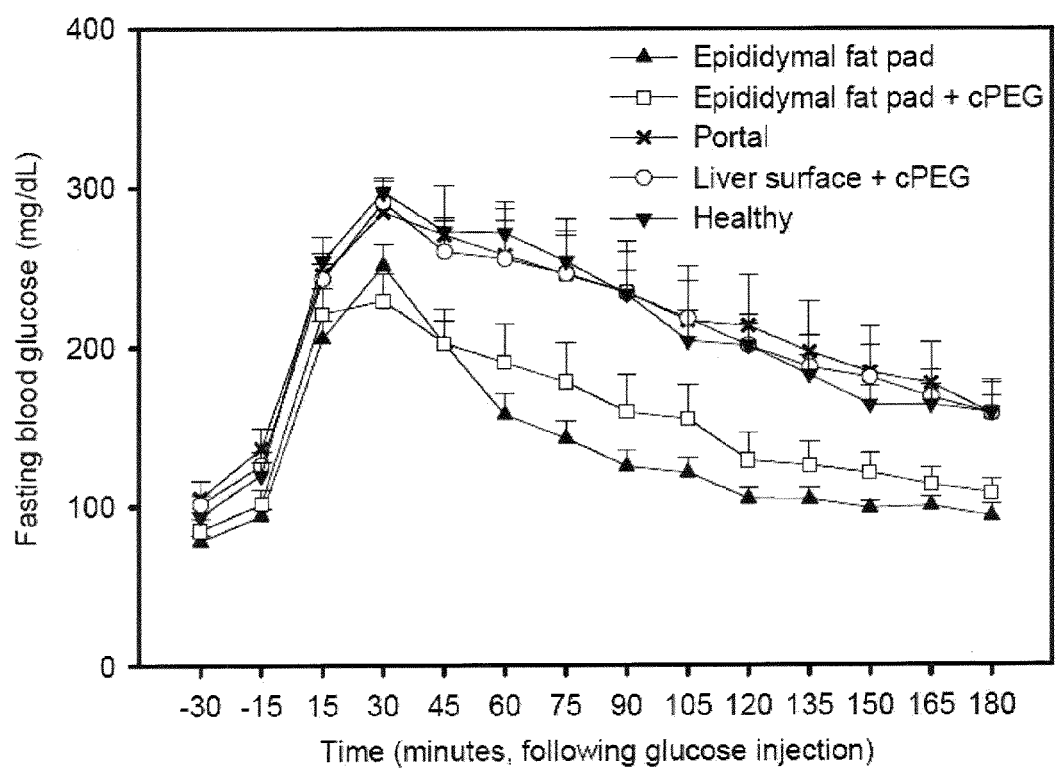
FIG. 7. Real-time graft performance in intraperitoneal glucose tolerance test. (a) Mean fasting blood glucose over time, following intraperitoneal injection of 10% glucose. Test groups were composed of normoglycemic mice previously transplanted at the sutured epididymal fat pad (▲, n=7); at the epididymal fat pad with adhesive immobilization (□, n=8); via intrahepatic portal delivery (x, n=7); at the liver surface with adhesive immobilization (○, n=8); as well as healthy untreated control mice (▼, n=5). (b) Integrated insulin response to intraperitoneal glucose injection, calculated by group. Asterisk (*) indicates statistical difference in mean area under blood glucose excursion curve (AUC) between the sutured epididymal fat pad and healthy control groups ($p<0.05$).
Figure 7B:
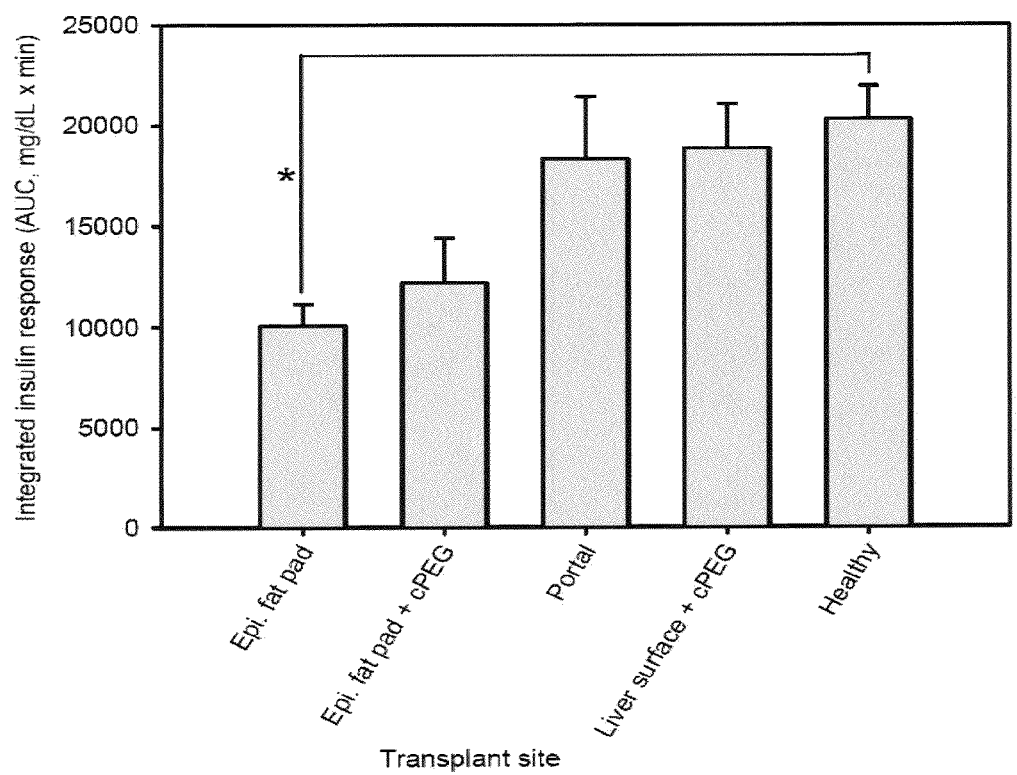

Intraperitoneal glucose tolerance test. To assess islet graft response to elevated blood glucose in real time, and to establish prolonged adhesive non-interference with transplanted islet function, an intraperitoneal glucose tolerance test was performed at 105 days post-transplant. Prior to injection, all groups displayed similar baseline blood glucose levels following 4-h fast. Blood glucose levels rose immediately following injection, peaked at 30 min in all groups, and fell over time with islet graft response (FIG. 7a). The area under the excursion curve (AUC), also known as the integrated insulin response, was significantly less for the sutured epididymal fat pad group compared to healthy controls. Otherwise, there was no statistical difference in AUC values among the remaining groups (FIG. 7b).

Figure 8:
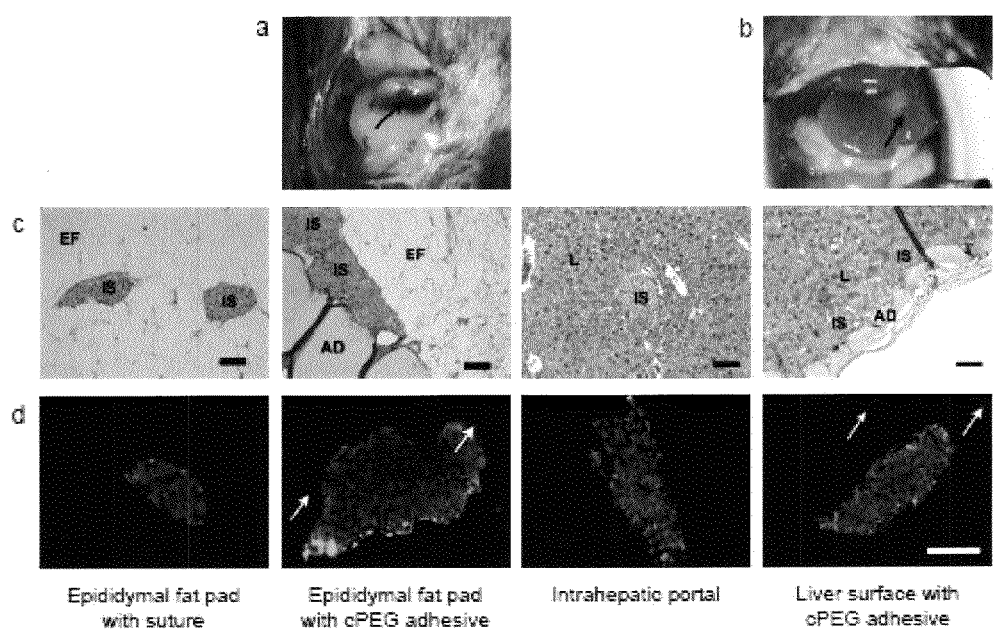
FIG. 8. Analysis of islet graft and cPEG adhesive explants. Top row: photographic images of the site of cPEG adhesive-mediated 150-islet transplantation at the epididymal fat pad and liver surface, immediately prior to graft explant on day 112. Immobilized islet bolus is visible on the external liver surface. Black arrows, cPEG adhesive. Middle row: representative light micrographs of hematoxylin and eosin (H&E)-stained graft explants. Adhesive, AD; islet, IS; epididymal fat tissue, EF; liver tissue, L. Scale bars: 100 mm. Bottom row: representative fluorescent micrographs of immunohistochemical triple stain of graft explants. Insulin, green; OX-41 (macrophage marker), blue; CD31 (endothelial cell marker), red. White arrows, non-specific cPEG labeling. All images, scale bar: 100 μm.
Figure 11:
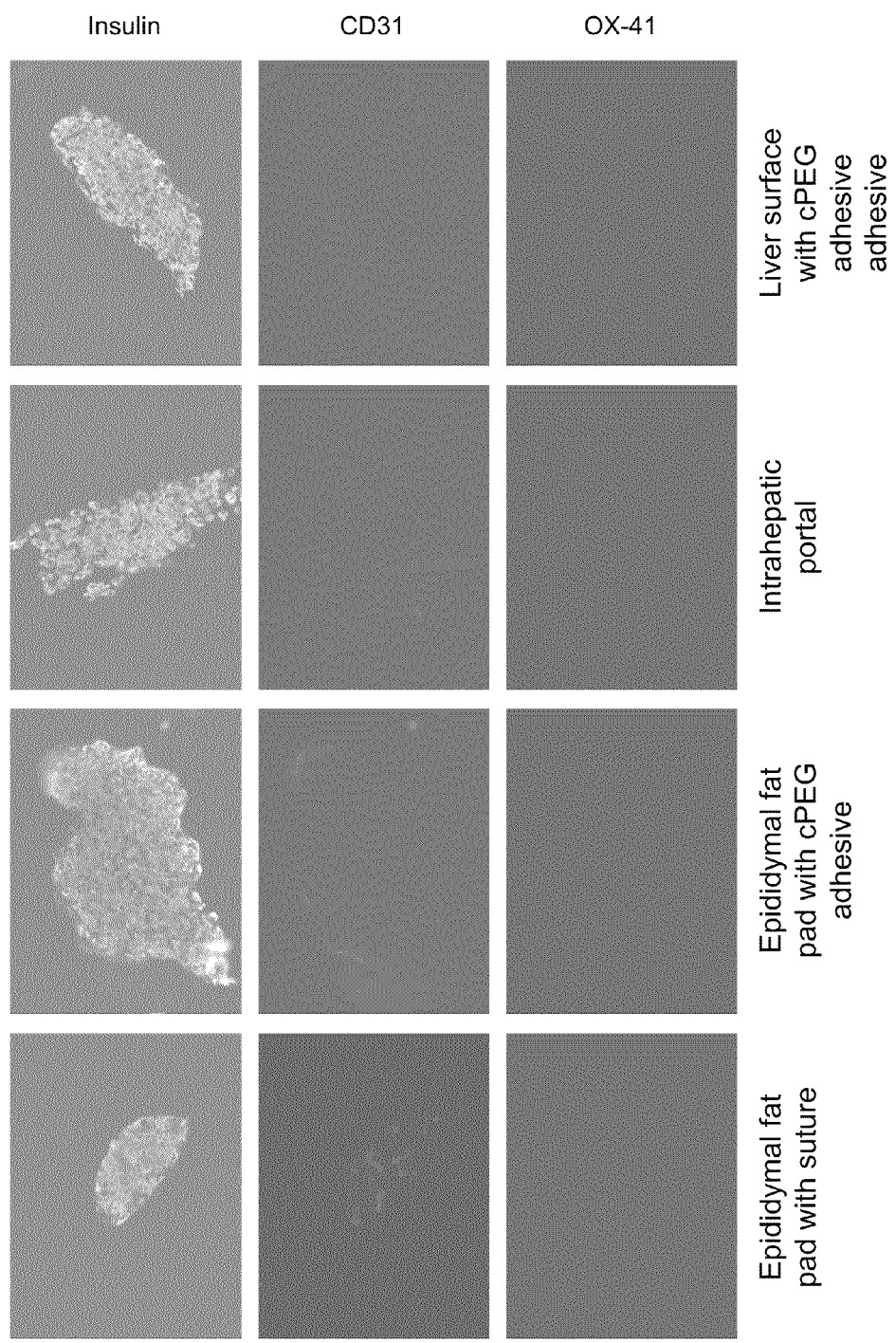
FIG. 11. Single-channel fluorescence images following triple-stain immunohistochemical identification of insulin (green, functional islet marker), CD31 (red, endothelial cell marker), and OX-41 (blue, macrophage marker).

Graft removal and histological analysis. At 112 days post-transplant, islet grafts with associated adipose tissue were removed from sutured epididymal fat pad and epididymal fat pad with adhesive recipient groups. Similarly, graft explants were collected through partial lobectomy for analysis of cPEG immobilized islets at the external liver surface. The applied adhesive was visible at the epididymal fat pad and liver surfaces (FIG. 8, top row), and was removed intact with the tissue graft. All mice survived explant surgery, which resulted in immediate hyperglycemia in these two groups as well as the sutured epididymal fat pad control group (FIG. 9a). On day 118, whole organ removal provided tissue samples of intraportally-delivered islets distributed in the liver vasculature. H&E staining of explant samples from all four groups showed intact, rounded islet architecture and direct islet contact with recipient tissue surfaces (FIG. 8, middle row). At the epididymal fat pad and liver surfaces, cPEG maintained intimate fixation to islets and recipient tissues and induced minimal inflammatory response. Immunohistochemical triple-stain analysis was performed on explant samples, for the identification of insulin-producing functional islets, infiltrating macrophages, and vascular endothelial cells (FIG. 8, bottom row; FIG. 11). There was no qualitative difference in intra-islet insulin production (green FITC signal) among the transplant groups. Little to no OX-41 signal indicated minimal macrophage infiltrate, but some non-specific labeling of the cPEG adhesive is observed (disperse blue AMCA signal).

Figure 9:
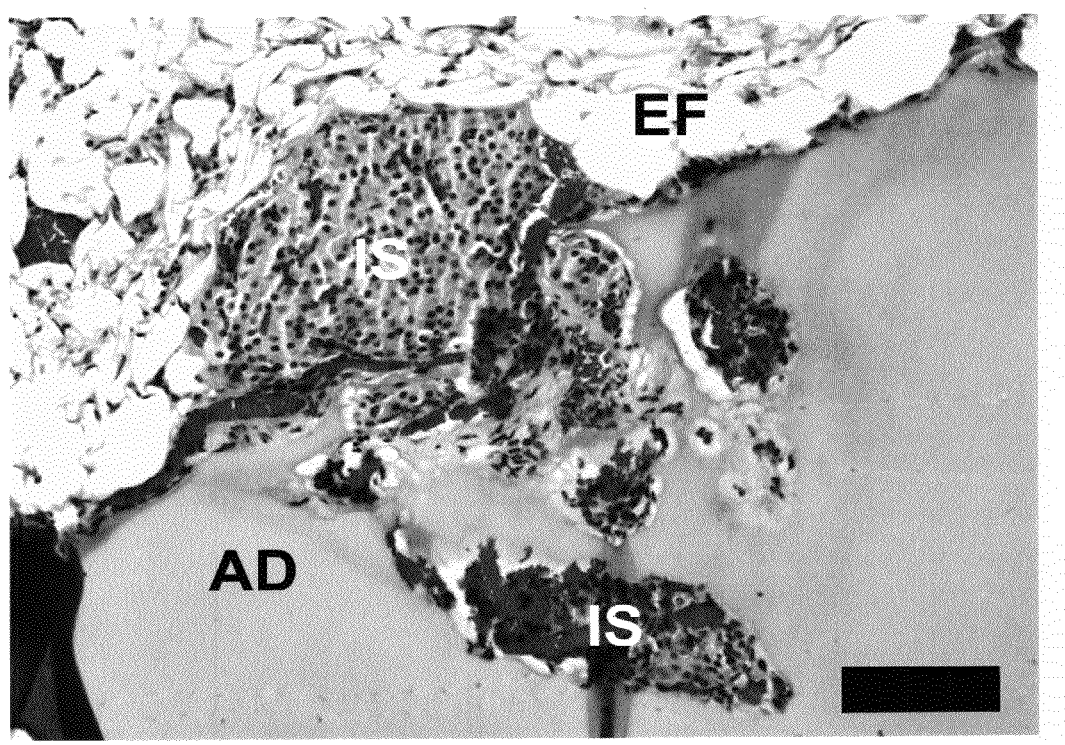
FIG. 9. Light micrograph of hematoxylin and eosin (H&E)-stained tissue explant demonstrating cPEG adhesive-mediated islet attachment and revascularization at the epididymal fat pad surface. Graft was removed at day 100 following transplantation. Adhesive, AD; islet, IS; epididymal fat tissue, EF.

In a representative image following minimal islet transplantation at the epididymal fat pad with suture (FIG. 8, bottom row, left panel), OX-41 signal has co-localized with CD31 labeling (Texas red), which identifies intra-islet endothelial cells. Due to limitations of triple-stain immunohistochemistry, CD31 endothelial cell marker signal was restricted in the remaining images; nevertheless, it is possible to identify islet blood supply from histology alone (FIG. 8). More explicitly, FIG. 9 shows H&E-stained, day 100 tissue explant sample from islets transplanted to the epididymal fat pad with cPEG immobilization, in which red erythrocytes are clearly visible in the peri- and intra-islet environment.

Discussion. In this study, we prepared an adhesive hydrogel material through chemical cross-linking of a catechol-terminated, PEG-based precursor and demonstrated its application in the murine model of syngeneic minimal islet transplantation. To generate the precursor, 3,4-dihydroxyhydrocinnamic acid (DOHA) was selected as the PEG modifying agent: this DOPA analog contains the catechol moiety essential for cross-linking and interfacial bonding, but lacks the primary amine of the DOPA amino acid, simplifying precursor synthesis and purification.

Previous studies of DOPA-terminated branched PEG under similar cross-linking conditions showed that gel formation and color change are due to catechol oxidation and subsequent cross-linking reactions that give rise to a polymer hydrogel network. For future clinical applications, the color change represents a desirable material attribute, as it permits visualization of the applied adhesive on tissue surfaces. Similar cPEG adhesive behavior was observed both in-vitro and in-vivo, even in the presence of biologically relevant fluids such as normal saline and islet culture media, highlighting the rapid, mussel-inspired wet adhesive nature of the cPEG material.

Adhesive performance was first examined in the absence of donor islets, at the epididymal fat pad of male mice. Tissue and cPEG removal surgeries were performed at time points relevant to the acute and chronic inflammatory response, following which explant histology confirmed minimal adhesive-stimulated inflammation. The persistence of cPEG adhesive interface with the epididymal fat pad, extending to one year, underscores the material's utility in adhesive applications requiring prolonged performance. The intimate interface between cPEG hydrogel and tissue likely reflects the presence of covalent bonds between the two, formed during solidification of the adhesive. It was previously shown that the oquinone group—a reactive, oxidized form of the catechol moiety that forms in the presence of periodate—covalently couples with primary amines. In addition, we surmise that o-quinone will also be reactive toward other nucleophiles such as thiols and imidazoles, resulting in broad reactivity toward residues found in ECM proteins of tissues. Such reactions likely form the basis of the continuous, intact adhesive/tissue interface observed in this study.

Islets are highly sensitive to chemical and physical insults; cPEG mediated minimal islet transplantation into streptozotocin-induced diabetic mice therefore represents a much more stringent test of material biocompatibility. We hypothesized that rapid, in-situ adhesive gelation would facilitate islet immobilization on the surface of alternative transplant tissue sites. This approach is minimally invasive to both islets and the recipient tissue and is best implemented on a highly vascular tissue, to allow rapid donor islet revascularization. In this study, we selected the epididymal fat pad and the external liver surface as candidate extrahepatic transplant sites. The epididymal fat pad is an easily-accessed, flexible adipose tissue flap chosen in light of previous syngeneic and allogeneic islet transplant studies at this site, whereas the liver surface represents a novel, previously untested site and the one most comparable to established intrahepatic islet delivery.

The sutured epididymal fat pad and intrahepatic sites were investigated as relevant controls. All experiments were performed in a syngeneic mouse model, in which the donor and recipient mice were genetically identical. That is, the experiment was designed to isolate the adhesive's influence on transplanted islet function without confounding by specific immune processes such as acute rejection. With the exception of mice transplanted at the external liver surface, no significant variation in mean time to normoglycemiawas observed among transplanted groups.

This result indicates that the cPEG material does not interfere with islet engraftment to the recipient epididymal fat pad surface. Further, all transplanted groups performed similarly in the intraperitoneal glucose tolerance test. IPGTT outcomes show that islet function in adhesive-mediated groups was comparable to function in healthy mice and in the clinically-relevant intrahepatic portal transplant site. This suggests that following normoglycemic recovery, the cPEG adhesive does not interfere with islets' real-time blood glucose sensing and insulin response. The adhesive-mediated approach may represent a viable alternative to more invasive and time-consuming epididymal fat pad suturing or intrahepatic portal delivery techniques.

Mean recovery time was significantly longer in mice transplanted with adhesive-immobilized islets at the liver surface. However, following recovery, this group performed similarly to other transplanted groups, including the epididymal fat pad with adhesive group. This may be attributed to recipient tissue architecture and surface characteristics, as opposed to limitations of the cPEG adhesive itself. Whereas the epididymal fat pad is a thin, flat tissue surface, the liver lobe is bulky and convex. Our observations with adhesive application on the external surface of the liver indicated that application of the viscous adhesive may have displaced some islets away from the deposition site; such islets are not expected to adhere to the tissue surface and may ultimately be lost into the intraperitoneal space. Given that the current study employed a minimal islet number (150), loss of islets from the implant site may result in delayed recovery time. We are currently investigating a spray applicator that may allow us to overcome this performance limitation.

At the conclusion of in vivo studies, immediate return to hyperglycemia following survival graft explant surgery confirmed that transplanted islets were responsible for diabetes reversal and ongoing normoglycemic maintenance. In the intrahepatic portal control group, widespread diffusion of islets in the liver vasculature renders partial lobectomy ineffective for removing all transplanted islets, and the essential nature of liver function to survival precluded whole liver organ removal. In this group it was therefore not possible to confirm the role of transplanted islets in normoglycemic recovery through whole organ explant surgery. Nevertheless, this tissue, with embolized islets, was obtained for histological analysis and comparison to other transplant sites.

At each transplant site, islets were present and intact, with obvious blood supply. Islet graft histology confirmed observations from the adhesive-only implant studies: at the site of deposition, the cPEG adhesive induced little to no inflammatory response at either the recipient tissue surface or the transplanted islet bolus. Immunohistochemical analysis confirmed healthy islet function at the time of graft removal and further demonstrated cPEG adhesive compatibility with transplanted islets and recipient tissues. Nearly total absence of infiltrating macrophages in cPEG-containing samples supported histological observations of minimal adhesive stimulated inflammatory cell infiltration. Observed diabetic recovery and ongoing normoglycemic control correlated with evidence of islet insulin production and revascularization, and indicated that adhesive immobilization does not interfere with these processes. In fact, this type of fixation may be vital to islet function, as islets freely transplanted in the intraperitoneal space are subject to limited revascularization/reinnervation and poor blood glucose sensing.

In our approach, the adhesive facilitated direct contact between islets and the recipient tissue surface, which may be advantageous to local re-establishment of islet vascularization. Indeed, the most probable origin of vascular infiltration is from this tissue surface, as the cPEG hydrogel forms a dense, long-lasting, and likely impenetrable bather to cellular migration from the intraperitoneal cavity. For the present and other envisioned applications, rapid cPEG cross-linking and tissue adhesion under physiologic conditions represent essential material characteristics. Though its robust wet/dry adhesive capabilities were inspired by DOPA catechol reactivity in mussel adhesive proteins, the material's PEG component also plays an important role in adhesive performance in the abdominal space. PEG-based materials have been utilized as synthetic islet immunoisolation barriers, shielding treated islets from elements of the host immune response.

However, islet encapsulation for the purpose of immunoisolation does not fully exclude low molecular weight inflammatory cytokines, while creating a physical barrier to revascularization and insulin secretion from entrapped islets. Rather than immunoisolation, the primary role of the cPEG adhesive in our method is to facilitate the direct apposition of islets to target recipient tissue surfaces. Interestingly, the free surface of solidified cPEG hydrogel is minimally adhesive to nearby tissues, as demonstrated by the complete absence of non-specific post-surgical adhesions in our in-vivo studies, even at the interface between the adhesive-coated liver surface and the abdominal wall. This attribute of cPEG hydrogels is likely a result of high PEG content and is favorable for use in the intraperitoneal cavity, given that non-specific adhesions to neighboring tissues or to the inner abdominal wall should be avoided.

This study provided valuable insight into the in vivo performance of mussel-mimetic cPEG hydrogel in the context of islet transplantation in mice. This cPEG adhesive provoked minimal inflammatory response and did not perturb islet architecture or glucose management, permitting a unique approach to murine islet transplantation through direct immobilization onto two-dimensional recipient tissue surfaces. The successful use of tissue-adherent hydrogel to immobilize islets onto the surface of extrahepatic tissues such as the liver and the epididymal fat pad overcomes disadvantages of existing islet transplantation techniques and supports broader investigation of the cPEG adhesive in islet transplantation and other surgical and biomedical applications.

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Deprest et al. Prenat Diagn 2008; 28:878-80.
2. Harrison et al. N Engl J Med 2003; 349:1916-24.
3. Devlieger et al. Am J Obstet Gynecol 2006; 195:1512-1520.
4. Zisch et al. Swiss Med Wkly 2008; 138:596-601.
5. Quintero R A. Clin Perinatol 2003; 30:573-89.
6. Quintero R A. Clin Perinatol 2001; 28:861-75.
7. Chang et al. J Pediatr Surg 2006; 41:905-9.
8. Young et al. Fetal Diagn Ther 2004; 19:296-300.
9. Mallik et al. Obstet Gynecol 2007; 110:1121-9.
10. Ochsenbein-Kolble et al. Am J Obstet. Gynecol 2007; 196:263 e1-7.
11. Petratos et al. Lasers Surg Med 2002; 30:48-53.
12. Cortes et al. Am J Obstet Gynecol 2005; 193:1197-203.
13. Reddy et al. Am J Obstet Gynecol 2001; 185:1090-3.
14. Louis-Sylvestre et al. Am. J. Obstet. Gynecol. 1998; 178:287-93.
15. Gratacos et al. Placenta 2006; 27:452-6.
16. Liekens et al. Prenat. Diagn. 2008; 28:503-7.
17. Papadopulos et al. Fetal Diagn. 2006; 21:494-500.
18. Leggat et al. ANZ J. Surg. 2007; 77:209-13.
19. Burke et al. Biomed. Mater. 2007; 2:203-10.
20. West et al. Proc Natl. Acad. Sci. USA 1996; 93:13188-93.
21. Johns et al. J Am Assoc Gynecol. Laparosc. 2003; 10:334-8.
22. Mettler et al. Fertil. Steril. 2004; 82:398-404.
23. Gillinov et al. J Card Surg 2001; 16:255-7.
24. McLaren et al. Hum Reprod 1999; 14:237-41.
25. Ferland et al. Hum Reprod 2001; 16:2718-23.
26. Lee et al. Biomacromolecules 2002; 3:1038-47.
27. Brubaker et al. Biomaterials 2010; 31:420-427.
28. Lee et al. Nature 2007; 448:338-41.
29. Lee et al. Proc Natl Acad Sci USA 2006; 103:12999-3003.
30. Lee et al. Surg Innov 2005; 12:203-13.
31. Oyen et al. Am J Obstet Gynecol 2006; 195:510-5.
32. Hill-West et al. Proc Natl Acad Sci USA 1994; 91:5967-71.
33. Lee et al. Science 2007; 318:426-30.
34. Waite et al. Ann N Y Acad Sci 1999; 875:301-9.
35. Yamada et al. Biomacromolecules 2000; 1:252-8.
36. Deming et al. Curr Opin Chem Biol 1999; 3:100-5
37. Devlieger et al. Eur J Obstet Gynecol Reprod Biol 2000; 92:145-50.
38. Spotnitz et al. Transfusion (Paris) 2008; 48:1502-16.
39. Waite, Integr Comp Biol 2002; 42:1172-80.
40. Waite, Science 1981; 212:1038-40.
41. Papov et al., J Biol Chem 1995; 270:20183-92.
42. Waite et al., Biochemistry 2001; 40:2887-93.
43. Burzio et al., Biochemistry 2000; 39:11147-53.
44. Yu et al., J Am Chem Soc 1999; 121:5825-6.
45. Lee et al., Proc Natl Acad Sci USA 2006; 103:12999-3003.
46. Lee et al. Biomacromolecules 2002; 3:1038-47.
47. Shao et al., Macromol Biosci 2009; 9:464-71.
48. Wang et al., Biomaterials 2007; 28:3456-68.
49. Westwood et al., Macromolecules 2007; 40:3960-4.
50. Yin et al., Biomaterials 2009; 30:2764-73.
51. Yu et al. Macromolecules 1998; 31:4739-45.
51. Hu et al., J Am Chem Soc 2003; 125:14298-9.
52. Tatehata et al., J Appl Polym Sci 2000; 76:929-37.
53. Burke et al., Biomed Mater 2007; 2:203-10.
54. Notkins, J Biol Chem 2002; 277:43545-8.
55. Shapiro et al., N Engl J Med 2000; 343:230-8.
56. van der Windt et al., Xenotransplantation 2007; 14:288-97.
57. Moberg et al., Clin Exp Immunol 2005; 142:125-31.
58. Bennet et al., Ups J Med Sci 2000; 105:125-33.
59. Barshes et al., J Leukoc Biol 2005; 77:587-97.
60. Shapiro et al., N Engl J Med 2006; 355:1318-30.
61. Ryan et al., Diabetes 2005; 54:2060-9.
62. van der Windt et al., Cell Transplant 2008; 17:1005-14.
63. Merani et al., Br J Surg 2008; 95:1449-61.
64. Elsner et al., Diabetologia 2000; 43:1528-33.
65. Chen X et al., Transplantation 2007; 84:122-5.
66. Dufour et al., Tissue Eng 2005; 11:1323-31.
67. Chen et al., Transplantation 2006; 81:1421-7.
68. Fritschy et al., Transplantation 1991; 52:777-83.
69. Cruise et al., Cell Transplant 1999; 8:293-306.
70. Cheung et al., Bioconjug Chem 2006; 17:1036-42.
71. Yun et al., Biomaterials 2007; 28:1957-66.
72. Wilson et al., Nano Lett 2008; 8: 1940-8.
73. de Groot et al., J Surg Res 2004; 121:141-50.
74. Weber et al., J Biomed Mater Res A 2008; 90:720-9.

We claim:

1. A method for repairing damage to a fetal membrane comprising contacting a fetal membrane with a composition comprising a four-armed catechol-terminated polyethylene glycol (cPEG) and a biocompatible oxidant.

2. The method of claim 1, wherein the four-armed cPEG and the biocompatible oxidant are initially contained in separate solutions, and wherein the solutions are mixed to form the composition just prior to or at the same time that the composition contacts the fetal membrane.

3. The method of claim 2, wherein the step of contacting the fetal membrane with the composition is performed using a double barrel syringe mixer/applicator to mix and direct the composition onto the fetal membrane tissue.

4. The method of claim 3, wherein before the composition is applied to the fetal membrane tissue, the solution containing the four-armed cPEG is added to one barrel of the syringe mixer/applicator, and the solution containing the oxidant is added to the other barrel of the mixer/applicator.

5. The method of claim 1, wherein the four-armed cPEG has the structural formula:

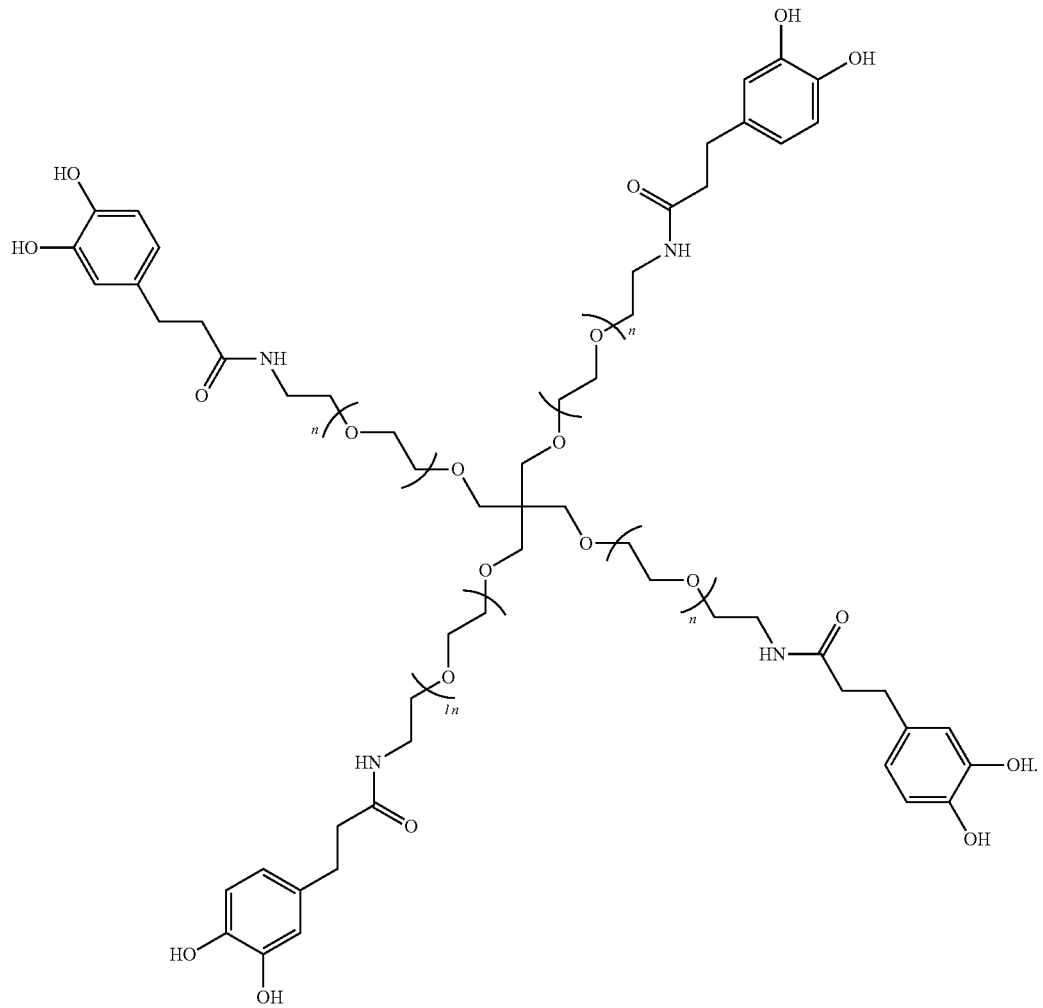

6. The method of claim 5, wherein n is 55.

7. The method of claim 1, wherein the oxidant is sodium iodate, Iron (III) chloride, a peroxide, oxygen, an inorganic base, an organic base, or an oxidase.

8. The method of claim 1, wherein the oxidant is a periodate.

9. The method of claim 8, wherein the periodate is sodium periodate.

10. The method of claim 1, wherein the composition further comprises an aqueous buffer solution.

11. The method of claim 10, further comprising the step of dissolving the four-armed cPEG in the aqueous buffer solution before the composition is contacted with the fetal membrane tissue.

12. The method of claim 1, wherein the method is performed immediately before, during, or immediately after fetal endoscopic surgery.

13. The method of claim 12, wherein the composition is contacted with the fetal membrane at the endoscopic access site.

* * * * *